US011160492B2

(12) United States Patent
Butterworth

(10) Patent No.: US 11,160,492 B2
(45) Date of Patent: Nov. 2, 2021

(54) FINGER INSERTS FOR A NAILFOLD IMAGING DEVICE

(71) Applicant: Massachusetts Institute of Technology, Cambridge, MA (US)

(72) Inventor: Ian Butterworth, Somerville, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 16/882,966

(22) Filed: May 26, 2020

(65) Prior Publication Data

US 2021/0022665 A1    Jan. 28, 2021

Related U.S. Application Data

(60) Provisional application No. 62/878,011, filed on Jul. 24, 2019.

(51) Int. Cl.
*A61B 5/00*        (2006.01)
*A61B 5/026*      (2006.01)
(Continued)

(52) U.S. Cl.
CPC ............ *A61B 5/449* (2013.01); *A61B 5/0077* (2013.01); *A61B 5/0082* (2013.01);
(Continued)

(58) Field of Classification Search
CPC ... A61B 5/0077; A61B 5/0082; A61B 5/6826; A61B 2562/146; A61B 2562/164;
(Continued)

(56) References Cited

U.S. PATENT DOCUMENTS 534,211 A      2/1895   English
2,588,528 A *   3/1952   Howser .................. D05B 91/04
                                              223/101
(Continued)

FOREIGN PATENT DOCUMENTS

CN         1108082 A      9/1995
CN         1342054 A      3/2002
(Continued)

OTHER PUBLICATIONS

Allen et al., "Computer based system for acquisition and analysis of nailfold capillary images," Medical Image Understanding & Analysis, (2003): 1-4.
(Continued)

*Primary Examiner* — Keith M Raymond
*Assistant Examiner* — Helene Bor
(74) *Attorney, Agent, or Firm* — Smith Baluch LLP

(57) ABSTRACT

A finger insert for use with a nailfold imaging device includes a housing to receive the user's finger and an immersion substance (e.g., immersion oil), and a deformable pad that holds the user's finger in place during imaging, as well as prevent bubble formation in the substance. The housing includes a transparent wall to facilitate imaging of the finger. The transparent wall includes multiple angled portions that prevent or reduce contact between the nailfold and the wall, to ensure sufficient blood flow through the nailfold region for imaging.

23 Claims, 24 Drawing Sheets
(16 of 24 Drawing Sheet(s) Filed in Color)

(51) Int. Cl.
*A61B 5/022* (2006.01)
*G06K 9/00* (2006.01)

(52) U.S. Cl.
CPC ........ *A61B 5/0261* (2013.01); *A61B 5/02241* (2013.01); *A61B 5/6826* (2013.01); *A61B 5/702* (2013.01); *A61B 2562/146* (2013.01); *A61B 2562/16* (2013.01); *A61B 2562/164* (2013.01); *A61B 2562/168* (2013.01); *G06K 2009/0006* (2013.01)

(58) Field of Classification Search
CPC ....... A61B 5/44; A61B 5/0064; A61B 5/6835; A61B 5/702; A61B 2562/168; A61B 2562/16; A61B 5/0261; A61B 5/7203; A61B 5/489; A61B 5/1455; A61B 2576/02; A61B 5/02241; A61B 5/0408; A61B 5/02154; A61B 5/449; G06K 9/00919; G06K 2009/0006
See application file for complete search history.

(56) References Cited

U.S. PATENT DOCUMENTS

| | | | |
|---|---|---|---|
| 4,998,533 A | 3/1991 | Winkelman | |
| 5,068,536 A | 11/1991 | Rosenthal | |
| 5,077,476 A | 12/1991 | Rosenthal | |
| 5,086,229 A | 2/1992 | Rosenthal et al. | |
| 5,204,532 A | 4/1993 | Rosenthal | |
| 5,218,207 A | 6/1993 | Rosenthal | |
| 5,237,178 A | 8/1993 | Rosenthal et al. | |
| 5,362,966 A | 11/1994 | Rosenthal et al. | |
| 5,365,066 A | 11/1994 | Krueger, Jr. et al. | |
| 5,436,455 A | 7/1995 | Rosenthal et al. | |
| 5,452,717 A * | 9/1995 | Branigan ............ | A61B 5/6826 600/323 |
| 5,582,705 A | 12/1996 | Yeung et al. | |
| 5,596,987 A | 1/1997 | Chance | |
| 5,598,842 A | 2/1997 | Ishihara et al. | |
| 5,676,143 A | 10/1997 | Simonsen et al. | |
| 5,782,757 A | 7/1998 | Diab et al. | |
| 5,855,212 A * | 1/1999 | Walker ................ | A45D 29/007 132/73.5 |
| 5,926,261 A * | 7/1999 | Hoshino ............ | G06K 9/00013 356/71 |
| 5,934,278 A | 8/1999 | Ishihara et al. | |
| 5,983,120 A | 11/1999 | Groner et al. | |
| 6,041,247 A * | 3/2000 | Weckstrom .......... | A61B 5/6826 600/323 |
| 6,213,952 B1 | 4/2001 | Finarov et al. | |
| 6,246,786 B1 | 6/2001 | Nishikiori et al. | |
| 6,358,208 B1 | 3/2002 | Lang et al. | |
| 6,424,851 B1 | 7/2002 | Berman et al. | |
| 6,687,521 B2 * | 2/2004 | Sato .................. | A61B 5/14552 600/310 |
| 8,858,429 B2 | 10/2014 | Mizuyoshi et al. | |
| 9,984,277 B2 | 5/2018 | Castro-Gonzalez et al. | |
| 2001/0002431 A1* | 5/2001 | Gurley .................. | A61B 42/20 602/61 |
| 2005/0209514 A1 | 9/2005 | Oshima et al. | |
| 2005/0268369 A1 | 12/2005 | Santiago | |
| 2006/0060770 A1 | 3/2006 | Page et al. | |
| 2006/0161063 A1 | 7/2006 | Shau | |
| 2007/0092115 A1 | 4/2007 | Usher et al. | |
| 2007/0116345 A1 | 5/2007 | Peterson et al. | |
| 2007/0161877 A1 | 7/2007 | Arai et al. | |
| 2007/0260129 A1* | 11/2007 | Chin ................... | A61B 5/4362 600/323 |
| 2008/0079723 A1 | 4/2008 | Hanson et al. | |
| 2009/0005693 A1 | 1/2009 | Brauner et al. | |
| 2009/0018417 A1* | 1/2009 | Wang .................. | A61B 5/1455 600/316 |
| 2009/0093970 A1 | 4/2009 | Lewy et al. | |
| 2010/0104169 A1 | 4/2010 | Yamada | |
| 2010/0254582 A1 | 10/2010 | Liu et al. | |
| 2010/0292629 A1 | 11/2010 | Dacey, Jr. et al. | |
| 2010/0324407 A1 | 12/2010 | Pichon et al. | |
| 2011/0134426 A1 | 6/2011 | Kaduchak et al. | |
| 2011/0275908 A1 | 11/2011 | Baumann | |
| 2012/0269420 A1 | 10/2012 | Najarian et al. | |
| 2013/0011055 A1 | 1/2013 | You et al. | |
| 2013/0216119 A1 | 8/2013 | Baumgart | |
| 2013/0235949 A1 | 9/2013 | Jeckeln | |
| 2014/0038206 A1 | 2/2014 | Holmes et al. | |
| 2014/0085482 A1 | 3/2014 | Teich et al. | |
| 2014/0092377 A1 | 4/2014 | Liu et al. | |
| 2014/0160481 A1 | 6/2014 | Ahner et al. | |
| 2014/0232869 A1 | 8/2014 | May et al. | |
| 2014/0240667 A1 | 8/2014 | Uji et al. | |
| 2014/0249784 A1 | 9/2014 | Sankaran et al. | |
| 2014/0273076 A1 | 9/2014 | Adams et al. | |
| 2015/0169641 A1 | 6/2015 | Alldrin et al. | |
| 2016/0148038 A1* | 5/2016 | Castro-Gonzalez ........................ | A61B 5/6826 382/134 |
| 2017/0367459 A1* | 12/2017 | Yamasaki ................ | B41J 3/407 |
| 2018/0012359 A1 | 1/2018 | Prentasic et al. | |
| 2018/0098683 A1 | 4/2018 | Kikuchi et al. | |
| 2018/0211380 A1 | 7/2018 | Tandon et al. | |
| 2019/0139221 A1 | 5/2019 | Castro-Gonzalez et al. | |

FOREIGN PATENT DOCUMENTS

| | | |
|---|---|---|
| CN | 1399131 A | 2/2003 |
| EP | 0641542 A2 | 3/1995 |
| KR | 20130028484 A | 3/2013 |
| KR | 101273692 B1 | 6/2013 |
| WO | 0027276 A1 | 5/2000 |
| WO | 0122741 A2 | 3/2001 |
| WO | 2017127732 A1 | 7/2017 |

OTHER PUBLICATIONS

Anderson et al., "Computerized nailfold video capillaroscopy—a new tool for assessment of raynaud's phenomenon," J. Rheumatology 32.5 (2005): 841-848.

Bourquard et al., "Non-invasive detection of severe neutropenia in chemotherapy patients by optical imaging of nailfold microcirculation." Scientific reports 8.1 (2018): 1-12.

Bourquard, Aurélien, et al. "Analysis of white blood cell dynamics in nailfold capillaries." 2015 37th Annual International Conference of the IEEE Engineering in Medicine and Biology Society (EMBC). IEEE, 2015, 11 pages.

Brown et al., "Rigidity of Circulating Lymphocytes is Primarily Conferred by Vimentin Intermediate Filaments", The Journal of Immunology, 166.11 (2001): 6640-6646.

CS&E PCT Collaborative Search and Examination Pilot Upload Peer Contribution mailed Mar. 7, 2019, 58 pages.

Delgado-Gonzalo et al., "Spline-based framework for interactive segmentation in biomedical imaging," IRBM 34.3 (2013): 235-243.

Deneux et al., "A processing work-flow for measuring erythrocytes velocity in extended vascular networks from wide field high-resolution optical imaging data." Neuroimage 59.3 (2012): 2569-2588.

Doshi et al., "Computer-Aided Analysis of Nailfold Capillaroscopy Images." Handbook of Research on Trends in the Diagnosis and Treatment of Chronic Conditions. IGI Global, 2016. 146-158.

Drew, Patrick J., et al. "Rapid determination of particle velocity from space-time images using the Radon transform." Journal of computational neuroscience 29.1-2 (2010): 5-11.

Eden et al., "An automated method for analysis of flow characteristics of circulating particles from in vivo video microscopy," IEEE Transactions on Medical Imaging 24.8 (2005): 1011-1024.

Etehad Tavakol, Mahnaz, et al. "Nailfold capillaroscopy in rheumatic diseases: which parameters should be evaluated?." BioMed research international 2015 (2015).

Extended European Search Report in European Patent Application No. 15862463.5 dated Sep. 11, 2018, 7 pages.

(56) References Cited

OTHER PUBLICATIONS

Golan et al., "Noninvasive imaging of flowing blood cells using label-free spectrally encoded flow cytometry," Biomed Opt Express 3.6 (2012): 1455-1464.
Grassi et al., "Capillaroscopy: questions and answers." Clinical rheumatology 26.12 (2007): 2009. 8 pages.
Hofstee et al., "A multicentre study on the reliability of qualitative and quantitative nail-fold videocapillaroscopy assessment." Rheumatology 51.4 (2012): 749-755.
Hofstee et al., "A multicentre study on the reliability of qualitative and quantitative nail-fold videocapillaroscopy assessment," Rheumatology (2011): ker403.
Hollis et al., "Comparison of venous and capillary differential leukocyte counts using a standard hematology analyzer and a novel microfluidic impedance cytometer," PloS One 7.9 (2012): e43702. 8 pages.
Hou et al., "A computerized system of nail-fold capillaroscopy for dry eye disease diagnosis." Multidimensional Systems and Signal Processing 23.4 (2012): 515-524.
Huang et al., "'A SR-based radon transform to extract weak lines from noise images," in Proceedings Int Conf on Image Processing, Barcelona, Spain 1 (2003): 849-852.
International Search Report and Written Opinion in International Patent Application No. PCT/US18/56100 dated Mar. 7, 2019, 16 pages.
International Search Report and Written Opinion in International Patent Application No. PCT/US2020/034483 dated Aug. 4, 2020, 11 pages.
International Search Report and Written Opinion issued for PCT/US15/62487, dated Feb. 5, 2016. 13 pages.
Kaur et al., "Nailfold Capillaryscopy Techniques—A Review," IRACST—IJCSITS 2.2 (2012): 326-331.
Kim et al., "An original approach for quantification of blood vessels on the whole tumour section." Analytical cellular pathology 25.2 (2003): 63-75.
Lefford et al., "Nailfold capillary microscopy in connective tissue disease: a quantitative morphological analysis." Annals of the rheumatic diseases 45.9 (1986): 741-749.
MacLennan et al., "Finger-prick blood samples can be used interchangeably with venous samples for CD4 cell counting indicating their potential for use in CD4 rapid tests," AIDS 21.12 (2007): 1643-1645.
Mckay et al., "Imaging human blood cells in vivo with oblique back-illumination capillaroscopy." Biomedical Optics Express 11.5 (2020): 2373-2382.
Mckay et al., "Visualization of blood cell contrast in nailfold capillaries with high-speed reverse lens mobile phone microscopy." Biomedical Optics Express 11.4 (2020): 2268-2276.
Mercer et al., "Quantitative nailfold video capillaroscopy in patients with idiopathic inflammatory myopathy." Rheumatology 49.9 (2010): 1699-1705.
Moeini, Mohammad, et al. "Effects of anesthesia on the cerebral capillary blood flow in young and old mice." Multiphoton Microscopy in the Biomedical Sciences XV. vol. 9329. International Society for Optics and Photonics, 2015, 7 pages.
Mugii, et a., "Reduced red blood cell velocity in nail-fold capillaries as a sensitive and specific indicator of microcirculation injury in systemic sclerosis," Rheumatology 48.6 (2009): 696-703.
Murray et al., "The influence of measurement location on reliability of quantitative nailfold videocapillaroscopy in patients with SSc." Rheumatology 51.7 (2012): 1323-1330.
Nagy et al., "Nailfold digital capillaroscopy in 447 patients with connective tissue disease and Raynaud's disease." Journal of the European Academy of Dermatology and Venereology 18.1 (2004): 62-68.
Pablo-Trinidad et al., "Automated detection of neutropenia using noninvasive video microscopy of superficial capillaries." American journal of hematology 94.8 (2019): E219. 4 pages.
Pennarola et al.,"Nailfold capillroscopic monitoring as preventive medicine in subjects exposed to ionising radiation." 11th International Congress of the international Radiation Protection Association. 2004. 6 pages.
Rao et al., "Evaluation of a new point of care automated complete blood count (CBC) analyzer in various clinical settings," Clinica Chimica Acta 389.1-2 (2008): 120-125.
Reif et al., "Label-free imaging of blood vessel morphology with capillary resolution using optical microangiography." Quantitative imaging in medicine and surgery 2.3 (2012): 207. 6 pages.
Riva et al., "Blue field entoptic phenomenon and blood velocity in the retinal capillaries," JOSA 70.10 (1980): 1234-1238.
Russcher et al., "Evaluation of the HemoCue WBC DIFF system for point-of-care counting of total and differential white cells in pediatric samples," Ned Tijdschr Klin Chem Labgeneesk 38.3 (2013): 140-141.
Sainthillier et al.,"Skin capillary network recognition and analysis by means of neural algorithms." Skin Research and Technology 11.1 (2005): 9-16.
Shore, "Capillaroscopy and the measurement of capillary pressure." British journal of clinical pharmacology 50.6 (2000): 501-513.
Uji et al., "The source of moving particles in parafoveal capillaries detected by adaptive optics scanning laser ophthalmoscopy," Investigative Ophthalmology & Visual Science 53.1 (2012): 171-178.
Winkelman et al., "Noninvasive Blood Cell Measurements by Imaging of the Microcirculation," Am J Clin Pathol 113 (2000): 479-483.
Wu, Chih-Chieh, et al. "Accuracy evaluation of RBC velocity measurement in nail-fold capillaries." Microvascular research 81.3 (2011): 252-260.
Yap et al., "Mechanical deformation of neutrophils into narrow channels induces pseudopod projection and changes in biomechanical properties", Journal of Applied Physiology 98.5 (2005): 1930-1939.
Bezemer et al., "Validation of near-infrared laser speckle imaging for assessing microvascular (re) perfusion." Microvascular research 79.2 (2010): 139-143.
Cheng et al., "Non-invasive assessment of microvascular and endothelial function." JoVE (Journal of Visualized Experiments) 71 (2013): e50008. 8 pages.
Dobbe et al., "Measurement of functional microcirculatory geometry and velocity distributions using automated image analysis." Medical & biological engineering & computing 46.7 (2008): 659-670.
Extended European Search Report in European Patent Application No. 18867626.6 dated May 19, 2021, 8 pages.
Mengko et al., "Morphological characterization of nailfold capillaries." 2016 International Seminar on Intelligent Technology and Its Applications (ISITIA). IEEE, 2016. 6 pages.

* cited by examiner

1300

Receiving a finger of a user in a finger insert disposed in a nailfold imaging device 1310

Imaging a nailfold portion of the finger via the wall portion of the finger insert using the nailfold imaging device 1320

US 11,160,492 B2

FINGER INSERTS FOR A NAILFOLD IMAGING DEVICE

CROSS-REFERENCE TO RELATED APPLICATIONS

This application claims priority to U.S. Provisional Application No. 62/878,011 title "FINGER INSERTS FOR A NAILFOLD IMAGING DEVICE" filed Jul. 24, 2019, the entire disclosure of which is incorporated by reference.

STATEMENT OF SUPPORT

This invention was made with Government support under Grant No. U54 EB015403 awarded by the National Institutes of Health (NIH). The Government has certain rights in the invention.

BACKGROUND

White blood cells (WBCs, also referred to as leukocytes or leucocytes) are cells of the immune system that are involved in protecting the body against both infectious disease and foreign invaders. WBCs can exist not only in the blood, but also in the lymphatic system and tissues. Some conditions can trigger a response in the immune system and cause an increase in the number of WBCs (also referred to as WBC count). Other conditions can affect the production of WBCs by the bone marrow or the survival of existing WBCs in the circulation system. As these examples illustrate, various conditions can cause a change (either an increase or a decrease) of the number of circulating WBCs. Therefore, WBC count can be a relevant physiological parameter for the diagnosis, monitoring, and/or treatment of various conditions including, but not limited to, bacterial and viral infections (e.g., pneumonia or meningitis), bone marrow functionality associated with chemotherapy toxicity, and hematologic proliferative processes such as leukemia.

In current clinical practice, most of the tests to derive WBC count are performed with large-scale equipment in central clinical laboratories. Generally, these ex vivo tests are still invasive because blood samples are collected from a patient (usually a full vial of blood is needed for each test). These blood samples are then transported, queued, and analyzed in laboratory tests, thereby taking several days to receive any results. This procedure can be burdensome for patients who need regular WBC counts or for patients with emergent conditions as well as their care. In addition, due to the ex vivo nature of conventional blood tests, there can be a certain bias of some parameters owing to the inherent differences between the measurements and the true physiological properties.

Related U.S. patent publication nos. 2016/0148038 and 2019/0139221 generally disclose nailfold imaging devices that include a finger well, as illustrated in FIG. 1. The finger well 110 of the imaging device 100 accommodates the user's finger 120 in the imaging device 100 and contains optical immersion oil. The finger well 110 also includes a flat optical window 130, to allow for illumination and for time-lapse microscopic imaging of the nailfold region of the user's finger 120 through the optical window 130. In such a finger well design, the rigid housing that forms the finger well 110 can provide enough space to accommodate different finger sizes, but can leave a gap between the finger and the housing, allowing space for the finger to move easily. Even with the user's hand resting on the housing for stability, this can result in involuntary movement of the finger that can make video recordings and/or imaging difficult. One potential solution is to 'under-size' the finger well to reduce finger movement; however, this limits the range of finger sizes that the device can accommodate.

SUMMARY

A finger insert for a finger imaging device includes a housing an opening to receive a finger of a subject. The housing defines a landing region abuts against a distal phalange of the finger of the subject when the finger is placed into the finger insert via the opening. The housing holds a liquid to facilitate imaging of a nailfold of the finger of the subject, such that at least the distal phalange of the finger is immersed in the liquid when the liquid is present in the finger insert and as the finger is placed into the finger insert via the opening. The housing includes a first wall and a second wall, with the second wall being optically transparent to facilitate imaging of the nailfold of the finger. The finger insert further includes a deformable pad positioned on at least a portion of the first wall, to form an open-pore structure that fills a gap between the first wall and the finger of the user when the finger is inserted into the finger insert, and to reduce trapped air in the liquid when the liquid is present in the finger insert, during insertion and movement of the finger in the finger insert A system includes a finger imaging device including a light source, a detector, and a receptacle including an imaging window. The light source and the detector are optically coupled to the imaging window. The system also includes a finger insert, the finger insert being disposable in the receptacle. The finger insert includes a housing defining an opening an opening to receive a finger of a subject, and further defining a landing region that abuts against a distal phalange of the finger of the subject when the finger is placed into the finger insert via the opening, to hold a liquid to facilitate imaging of a nailfold of the finger of the subject. At least the distal phalange of the finger is immersed in the liquid when the liquid is present in the finger insert and as the finger is placed into the finger insert via the opening. The housing includes a first wall and a second wall, the second wall being optically transparent to facilitate imaging of the nailfold of the finger via the light source and detector. The finger insert further includes a deformable pad positioned on at least a portion of the first wall, to form an open-pore structure that fills a gap between the first wall and the finger of the user when the finger is inserted into the finger insert, and to reduce trapped air in the liquid when the liquid is present in the finger insert, during insertion and movement of the finger in the finger insert.

A kit includes a finger imaging device including a light source, a detector, and a receptacle including an imaging window. The light source and the detector are optically coupled to the imaging window. The kit also includes a set of finger inserts, each finger insert of the set of finger inserts being disposable in the receptacle such that at least a section of the second wall of that finger insert is in optical communication with the imaging window when that finger insert is disposed in the receptacle. A first finger insert of the set of finger inserts is different from a finger insert apparatus of the set of finger inserts in one or more of a length of the housing along its longitudinal axis, and an average cross-sectional area of a curved portion of the first wall.

A method includes receiving a finger of a user in a finger insert disposed in a finger imaging device. The finger insert includes a housing defining an opening an opening to receive a finger of a subject, and further defining a landing region abuts against a distal phalange of the finger of the subject when the finger is placed into the finger insert via the opening, to hold a liquid to facilitate imaging of a nailfold of the finger of the subject. At least the distal phalange of the finger is immersed in the liquid when the liquid is present in the finger insert and as the finger is placed into the finger insert via the opening. The housing including a first wall and a second wall, the second wall being optically transparent to facilitate imaging of the nailfold of the finger. The finger insert also includes a deformable pad positioned on at least a portion of the first wall, to form an open-pore structure that fills a gap between the first wall and the finger of the user when the finger is inserted into the finger insert, and to reduce trapped air in the liquid when the liquid is present in the finger insert, during insertion and movement of the finger in the finger insert. The method further includes imaging a nailfold portion of the finger via the wall portion of the finger insert using the finger imaging device.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The skilled artisan will understand that the drawings primarily are for illustrative purposes and are not intended to limit the scope of the inventive subject matter described herein. The drawings are not necessarily to scale; in some instances, various aspects of the inventive subject matter disclosed herein may be shown exaggerated or enlarged in the drawings to facilitate an understanding of different features. In the drawings, like reference characters generally refer to like features (e.g., functionally similar and/or structurally similar elements).

DETAILED DESCRIPTION

Figure 1:
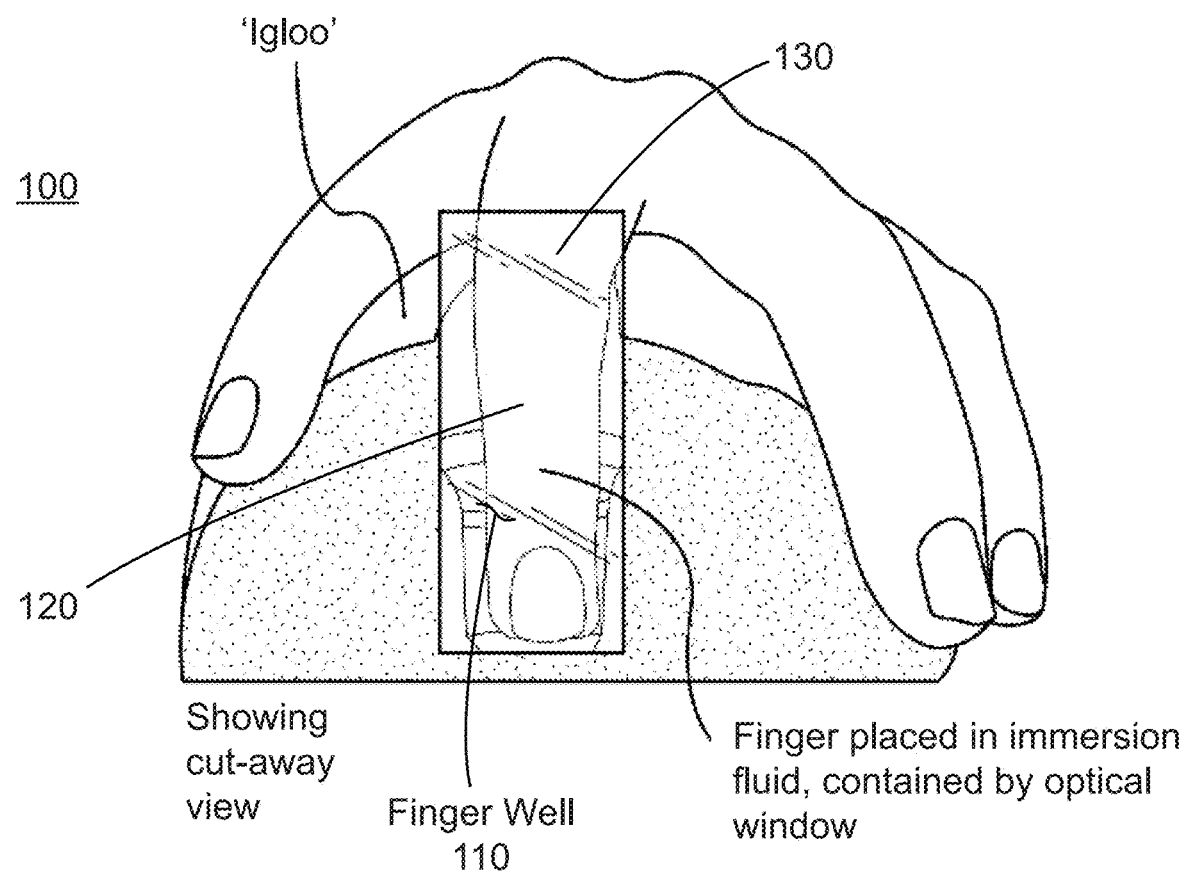
FIG. 1 is an illustration of conventional nailfold imaging with a user's finger disposed in a finger well.

Following below are more detailed descriptions of various concepts related to, and implementations of, kits, systems, devices, and methods that encompass finger inserts for nailfold imaging. It should be appreciated that various concepts introduced above and discussed in greater detail below may be implemented in numerous ways. Examples of specific implementations and applications are provided primarily for illustrative purposes to enable those skilled in the art to practice the implementations and alternatives apparent to those skilled in the art.

The figures and example implementations described below are not meant to limit the scope of the present implementations to a single embodiment. Other implementations are possible by way of interchange of some or all of the described or illustrated elements. Moreover, where certain elements of the disclosed example implementations may be partially or fully implemented using known components, in some instances only those portions of such known components that are necessary for an understanding of the present implementations are described, and detailed descriptions of other portions of such known components are omitted so as not to obscure the present implementations.

Generally, a finger insert as described herein can include and/or encompass a removable piece that is inserted into a nailfold imaging device before a measurement (e.g., imaging, video recording) starts, and is removed afterwards. In one aspect, the finger insert may be single-use and disposable, or reusable. In another aspect, the finger insert can be designed to engage with the nailfold imaging device ergonomically and securely, such that it provides a sturdy yet comfortable support for the finger while in use.

As described in greater detail later, the finger insert can include an incorporated optical window to ensure that the optical path between the imaging and illumination optics is clean and transparent each time. Immersion oil can be pre-filled into the finger insert to prevent re-use and contamination of immersion oils with particulates. The insert accommodates different finger sizes through variable internal geometry, with different sized inserts available (e.g., small-long, small-short, medium-long, medium-short, large-long, large-short).

In another aspect, the finger insert includes one or more flexible spacers to effectively and comfortably fill a gap that may be present between the rigid body of the finger insert and the finger of the subject. In one example discussed in further detail below, the flexible spacers may be implemented as rubber cylinders extruded from (and extending from) the walls of the body of the finger insert. In one aspect, the open-pore structure of the rubber cylinders significantly mitigates the trapping of air which would otherwise occur with semi-closed-pore structures like sponges, that would produce air bubbles in the immersion oil under the typical compression that occurs during inserting and movement of the finger.

Figure 2:
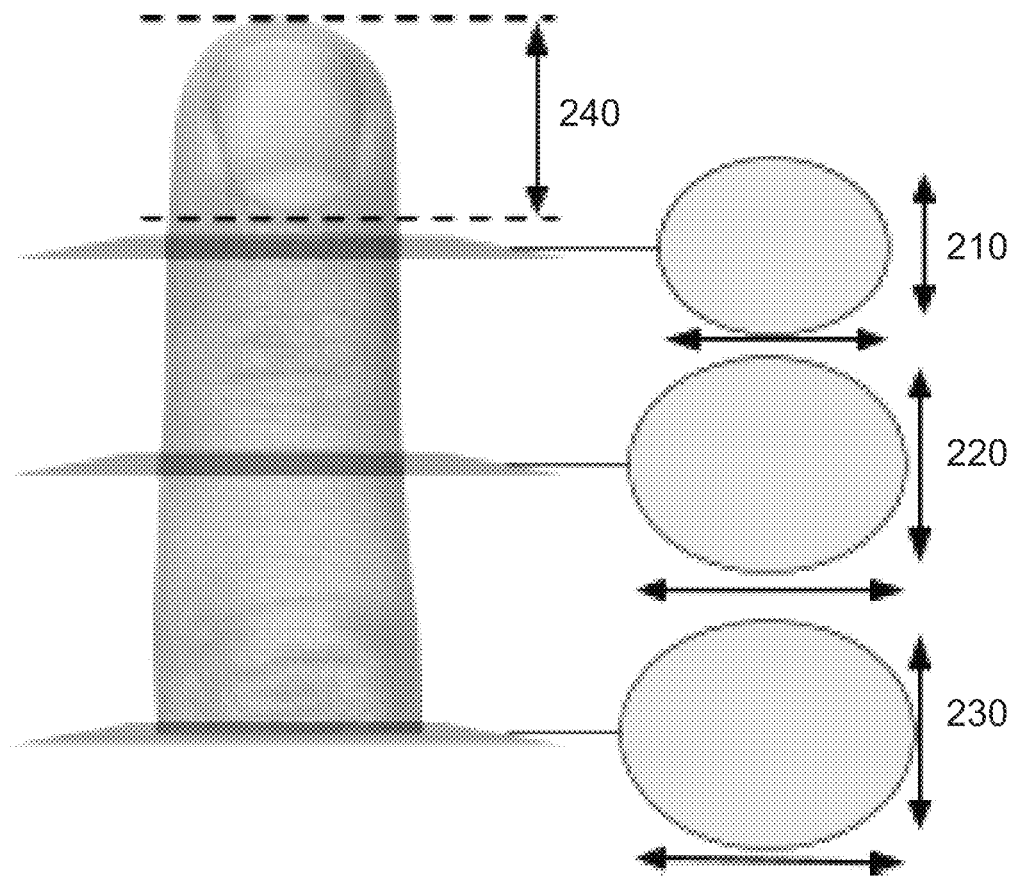
FIG. 2 illustrates example aspects and/or considerations for designing of a finger insert.

FIG. 2 illustrates aspects of finger geometry that can be considered when designing inventive finger inserts according to the present disclosure to accommodate various finger sizes. As a first example aspect, cross-sectional area and shape along the length of the finger (e.g., see the cross-sectional profiles 210, 220, 230 along the length of the finger) can affect how securely the finger fits into the opening in the finger insert, and also how much force is applied on the finger. Excessive force on the finger can result in restriction of blood flow (that could in turn impede measurement made on the nailfold capillaries of that finger), and too little support or restriction would reduce the necessary constraint for minimizing involuntary movement.

A second example aspect can be the length of the finger from fingertip to nailfold (e.g., the length 240), which is typically the same or similar to the fingernail length of that finger. The finger insert is designed such that the fingertip registers with the bottom of the insert, so that the distance between the end of the finger and the nailfold affects how high the nailfold sits in the well of the finger insert. This can be significant since the nailfold would need to fall within a region where the nailfold imaging device is able to image the nailfold region.

Figure 3:
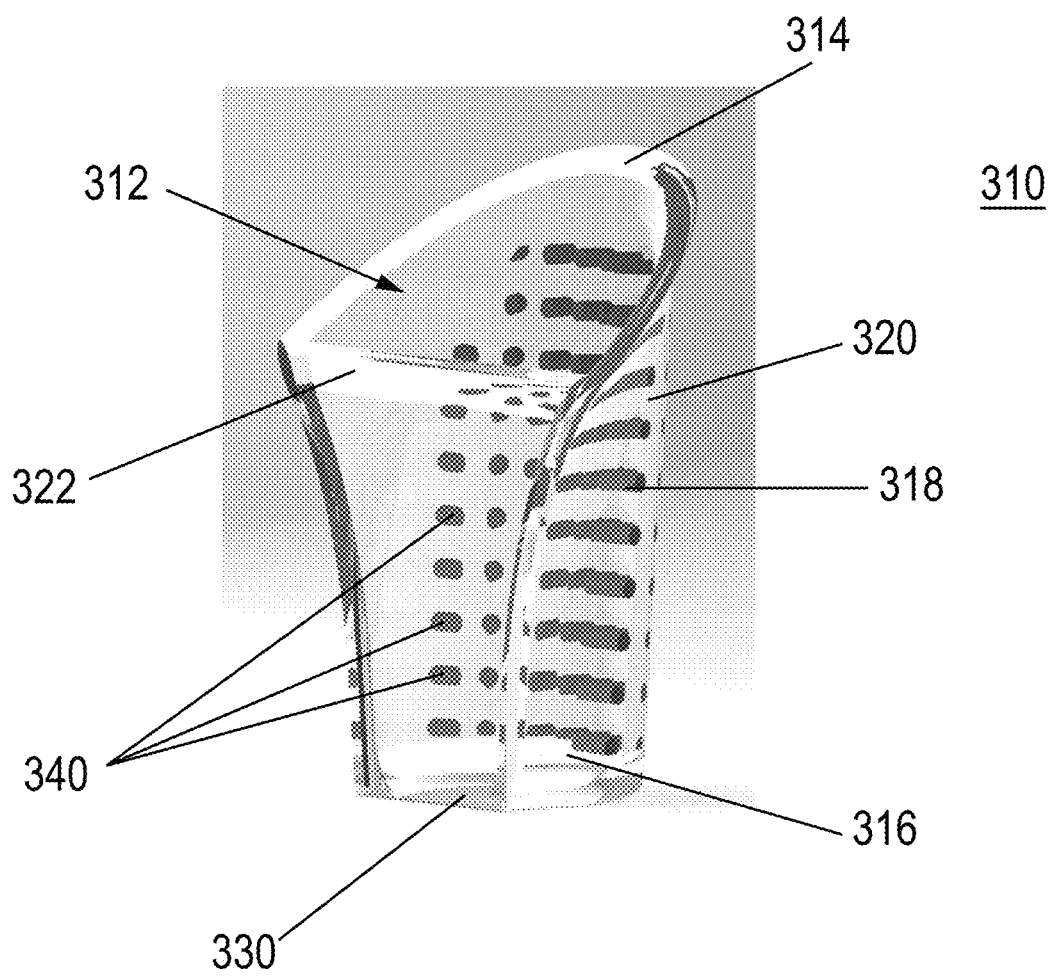
FIG. 3 illustrates an example finger insert.

FIG. 3 illustrates an example finger insert 310. The insert 310 can include a housing 312, a plate 330 (that may or may not be integrally formed with the housing), and multiple spacers 340 that are deformable by a user's finger when inserted into the insert 310. The housing 312 and the plate 330 can be made from a substantially rigid, inelastic material such as a transparent thermoplastic (e.g. Poly(methyl methacrylate), or PMMA). The spacers can be made from an elastic, deformable material such as a silicone. In some cases, the material of the spacers can be optically transparent, while it can be absorbing in some other cases.

The housing can include a top end 314 that has an opening to receive the user's finger, and a bottom end 316. A body 318 of the housing 312 is disposed and/or otherwise formed between the top end 314 and the bottom end 316, and can hold an immersion oil. The immersion oil can be selected to have a refractive index (e.g., a RI of about 1.51) that is similar to that of the housing and/or the dermis of the finger, to facilitate the nailfold imaging. The housing 312 can be sized to hold enough immersion oil such that at least the distal phalange of the finger is fully immersed in it. The housing 312 can include a curved portion 320 and a wall portion 322. The wall portion 322 can be optically transparent and substantially flat to prevent spurious reflections that can arise due to the illumination. In some cases the wall portion 322 can be curved, or another suitable form to conform to the nailfold imaging device during use.

The curved portion 320 can have a cross-sectional area (CSA) that (in at least a portion of the curved portion 320) continuously or discontinuously changes from the top end 314 to the bottom end 316. As explained above in connection with FIG. 2, such a CSA profile can accommodate for the typical changes in CSA of a user's finger along its length, towards the nailfold region. The curved portion 320 can be optically transparent, or absorbing to prevent reflection of a light beam from the light source of the nailfold imaging device.

The CSA can vary from about 3 cm$^2$ to about 1 cm$^2$ from the top end 314 to the bottom end 316. The depth of the housing from the top end 314 to the bottom end 316 can vary from about 10 mm to about 20 mm.

The plate 330 is disposed, attached, coupled and/or otherwise present at the bottom end 316 of the housing 312 and can abut against a distal phalange of the finger of the subject to position the finger for imaging. The plate 330 and the bottom end 316 can form a fluid-tight seal to prevent the immersion oil from leaking.

As also shown in FIG. 3, multiple, deformable spacers 340 can be positioned, attached, formed, and/or otherwise disposed on the curved portion 320. The number, size, shape, and/or other aspects of the spacers 340 can be useful for forming an open-pore structure that can effectively and significantly fill a gap between the curved portion 320 and the finger of the user when inserted. Further, the spacers 340 can be designed to accommodate a variety of finger geometries, with the goal of providing support to minimize unintentional movement during the measurement. Additionally, the open-pore structure of the spacers 340, even when deformed due to the pressure from the user's finger, significantly reduces or eliminates trapped air in the immersion oil when the user's finger is inserted into the insert, or moved around within the insert.

Figure 4:
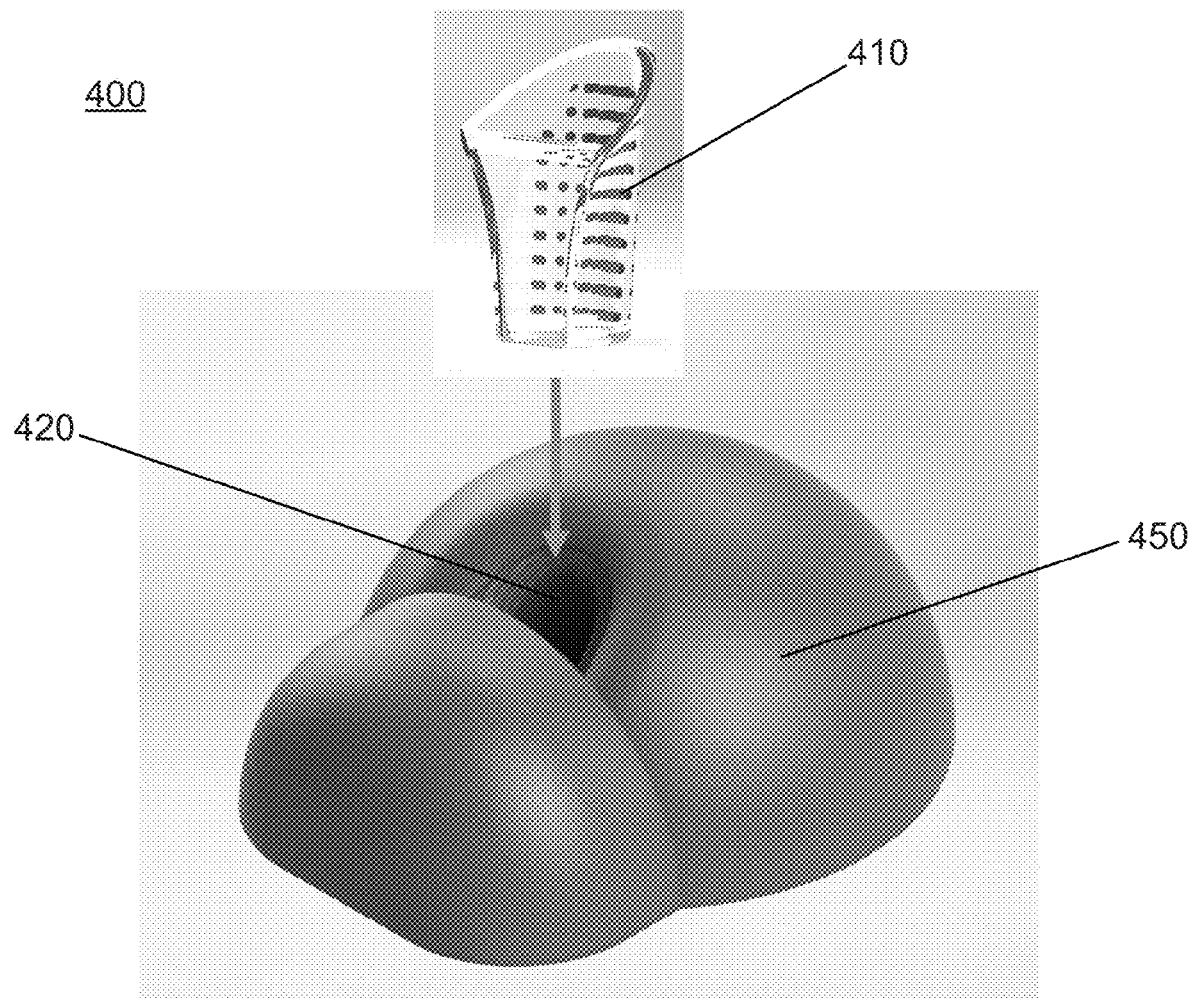
FIG. 4 illustrates the finger insert of FIG. 3 being inserted into a receptacle of a nailfold imaging device.
Figure 5:
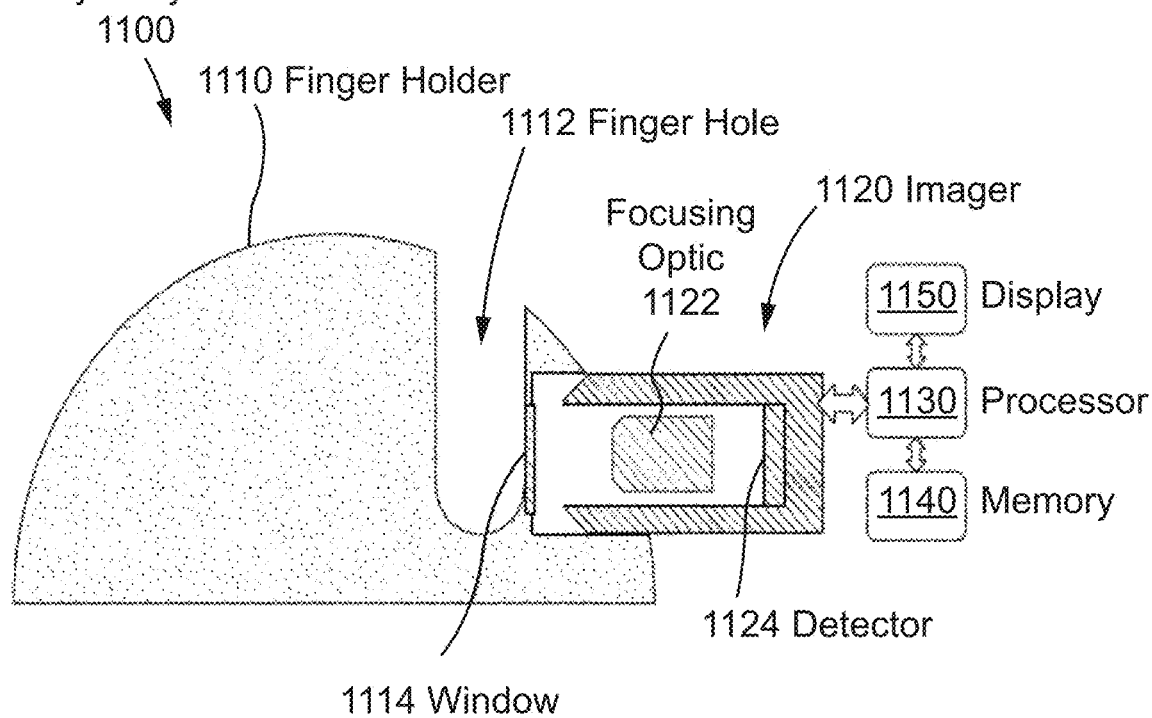
FIG. 5 illustrates details of a nailfold imaging device.

FIG. 4 illustrates a system 400 that includes a finger insert 410, which can be structurally and/or functionally similar to the insert 310. The system also includes a nailfold imaging device 450, which can be similar to such devices disclosed in the related U.S. patent publication nos. 2016/0148038 and 2019/0139221, the disclosures of which are incorporated herein by reference in their entirety. The insert 410 is inserted into a receptacle 420 of the device 450 to achieve a firm mating to allow for rigid mechanical coupling of the insert 410 and device 450, and to achieve a stable optical alignment for imaging the nailfold region of a finger in the insert 410. FIG. 5 generally illustrates an example nailfold imaging device 1100 (also referred to as a "WBC detection and analysis system") that includes a finger holder 1110 with a receptacle 1112 (also referred to as a "finger hold"). An imaging window 1114 is formed within the receptacle 1112 can be in optical communication with the interior of the insert 410 via its wall portion to permit nailfold imaging of the user's finger in the inert.

The device 1100 can include an imager/imaging setup 1120 that includes a light source (not shown) to illuminate the user's nailfold region within the insert 410 via the window 1114. The imager 1120 includes a focusing optic 1122 to collect light reflected or scattered from the finger and detector 1124 to receive the reflected or scattered light so as to form images of the finger. The device 1100 further includes a processor 1130 operably coupled to the imager 1120 and a memory 1140 operably coupled to the processor 1130. The memory 1140 is encoded with processor-executable instructions, which, when executed by processor 1130, may perform the methods described in the '038 and/or the '221 publications to analyze images received from the imager 1120. The device 1100 also includes a display 1150, which can display the images or videos taken by the imager 1120 and/or data associated with WBC events detected by the processor 1130.

Figure 6A:
FIG. 6A shows the finger insert of FIG. 3 without spacers and without immersion oil.
Figure 6B:
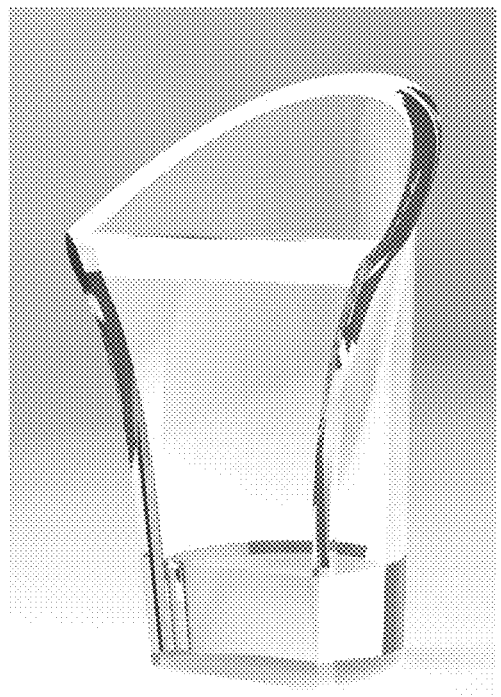
FIG. 6B shows the finger insert of FIG. 6A with some immersion oil added.

FIG. 6A shows the insert 310 without the spacers and without any immersion oil, and illustrates the optical clarity of the insert 310. FIG. 6B illustrates the insert of FIG. 3A with immersion oil added.

Figure 7A:
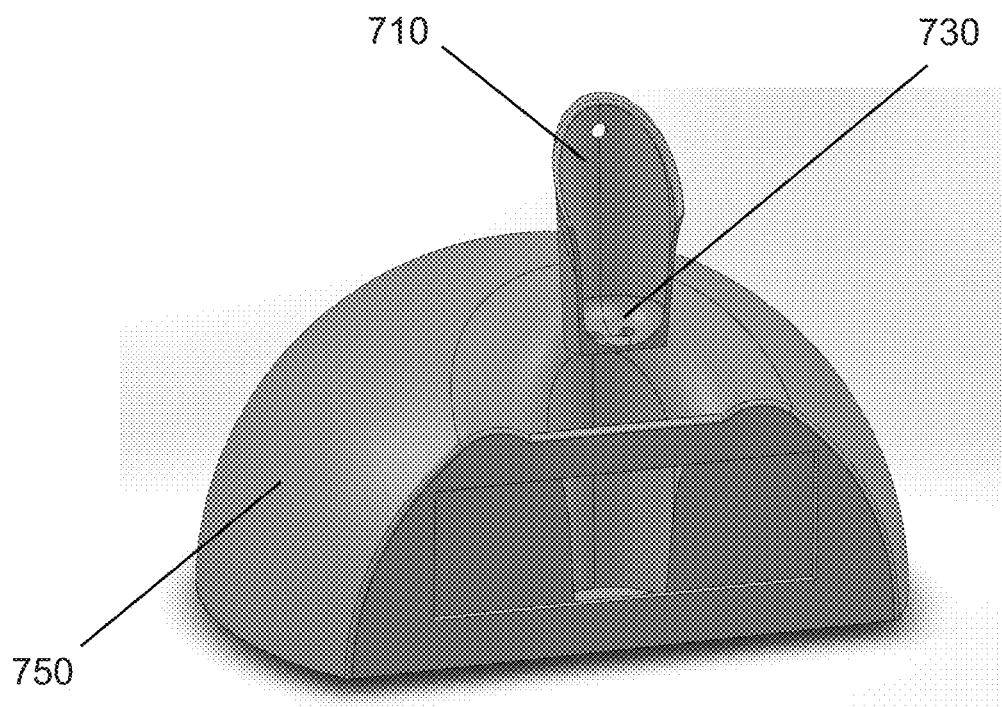
FIG. 7A shows another finger insert and a nailfold imaging device for receiving that insert, according to the present disclosure.

FIG. 7A illustrates another insert design, where insert 710 does not include the wall portion of the insert 310, and wherein the plate 730 has a relatively more rounded profile than the plate 330 to better conform to a user's fingertip, and to prevent inadvertent movement. In some cases, however, the plate 730 can be substantially flat.

Figure 7B:
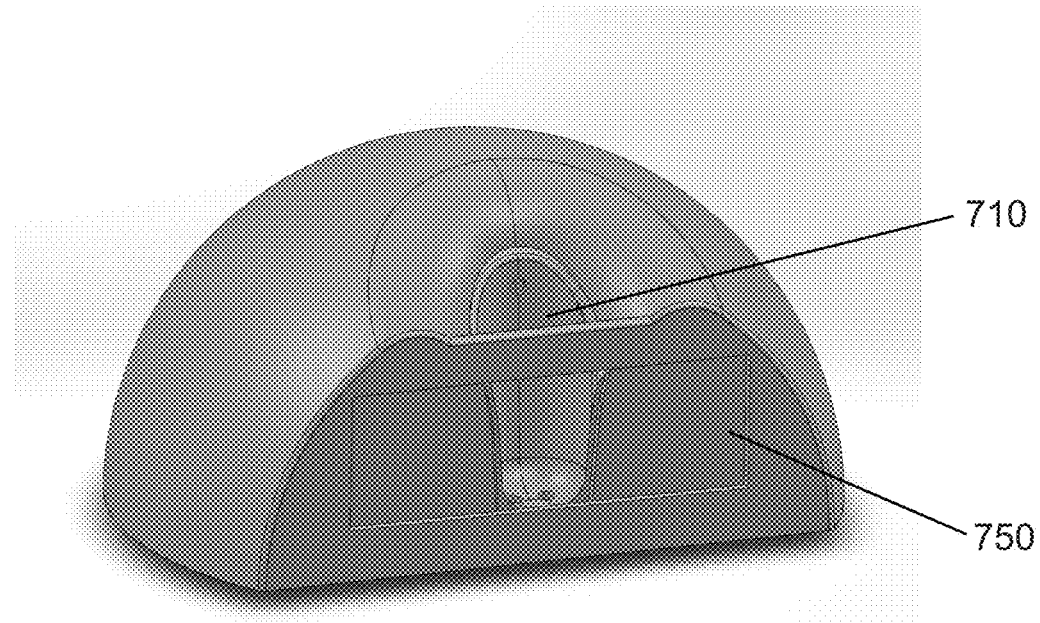
FIG. 7B shows the components of FIG. 7A with the insert positioned in the nailfold imaging device.

As illustrated in FIG. 7B, when the insert 710 is inserted into the nailfold imaging device 750 and immersion oil is added, the lack of the wall portion can provide for fewer coupling layers between the device and the user's finger, and a simplified design relative to that of the insert 310. Such a setup can require removal and replacement of immersion oil within the receptacle of the device 750, periodic cleaning to avoid accumulation of dirt and/or dust, and replacement of the imaging window (e.g., the window 1114) due to potential scratching over time, which can deteriorate imaging.

Aspects disclosed herein can also include a kit of finger inserts (e.g., the insert 310, 710, etc.). At least some of the inserts in the kit can be identical to each other, while in some cases, at least some of the inserts can be different in, for example, length of the housing, the cross-sectional profile of the curved portion, and so on. In this manner, the kit can include enough identical inserts for typical finger sizes and profiles, for repeated imaging thereof, and/or for varied finger sizes and profiles. In some cases, the kit can include the nailfold imaging device itself as well.

FIGS. 8A-8D illustrates a housing 820 of another finger insert design. The housing 820 includes an opening 830 through which a user can insert their finger into the housing. Upon insertion, the distal phalange of the finger of the user can land on and/or abut against a landing region 840 of the housing 820. The landing region 840, can generally form, at least in part, a curved socket that conforms to the shape of the tip of a typical human finger. The curved socket can be positioned to ensure that the user's finger lands landed approximately centered about a longitudinal axis A-A' of the housing 820 in the view illustrated in FIG. 8B.

Generally, the housing 820 can form a fluid-tight seal to hold a substance, e.g., an immersion oil or any other suitable liquid, to facilitate imaging. For example, the immersion oil can have a refractive index (e.g., a RI of about 1.51) that is similar to that of the housing 820 and/or the dermis of the finger, to facilitate the nailfold imaging. The housing 820 can be sized such that at least the distal phalange of the user's finger is within the housing 820, and can be immersed in the substance, to permit imaging of the nailfold region. For example, a length of the housing, such as along the axis A-A', can be from about 1 cm to about 7 cm, including all values and sub-ranges in between. The housing 820 can be wholly or partly formed of an inelastic material such as, for example such as an optically transparent thermoplastic (e.g. Poly(methyl methacrylate), or PMMA) glass (e.g., amorphous or crystalline), quartz (e.g., including Herkimer diamond, rock crystal, etc.), and/or the like. It is understood that imaging of the nailfold region can encompass imaging of at least some portion of the nailfold. For example, it is not required that the entire nailfold of the finger be exposed and/or otherwise available for imaging (e.g., due to the size of the imaging window of the imaging device), and imaging of the exposed portion of the nailfold can be sufficient for the purposes laid out herein, including for white blood cell measurements.

Figure 8A:
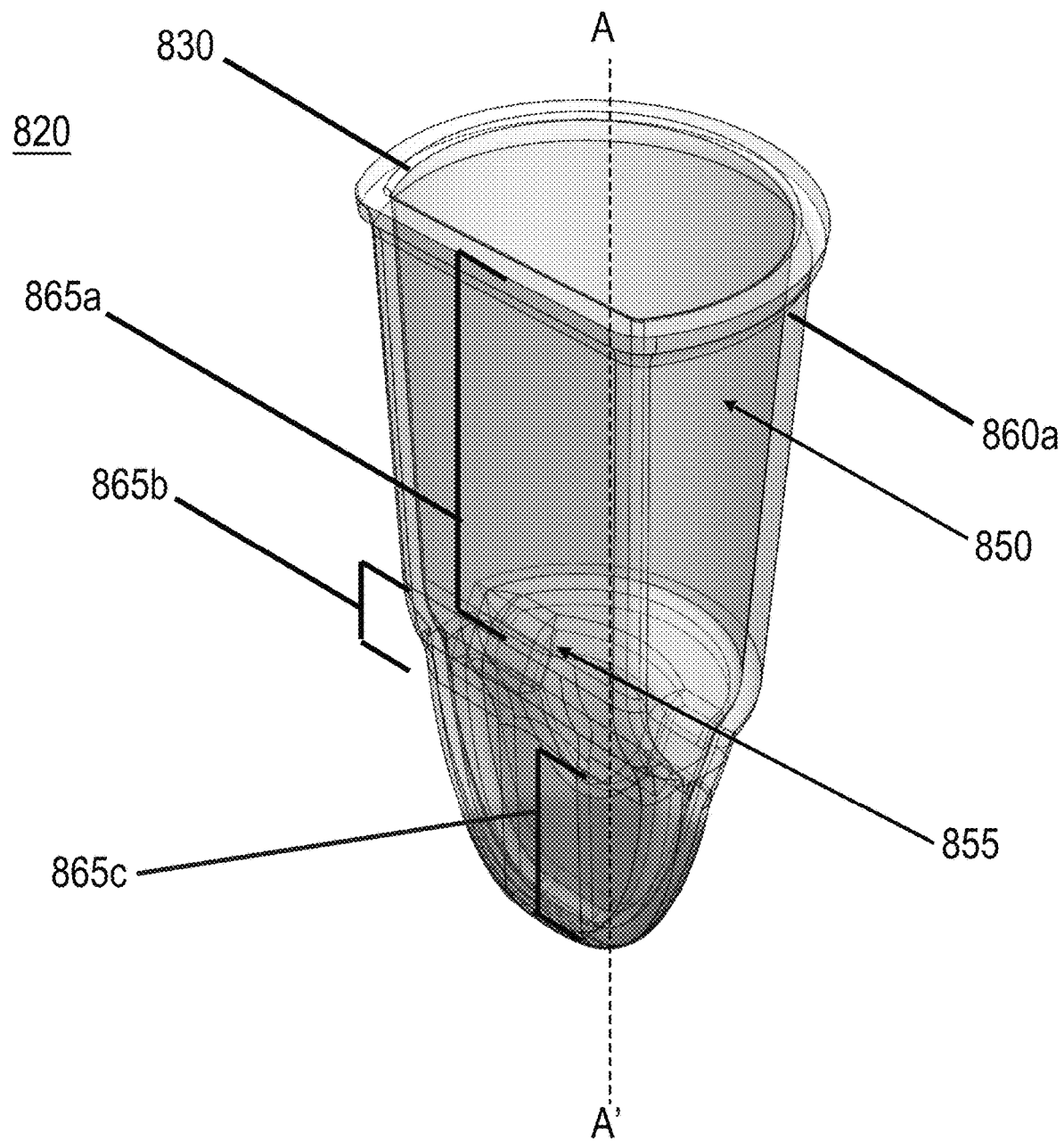
FIG. 8A illustrates a perspective view of another example finger insert.
Figure 8B:
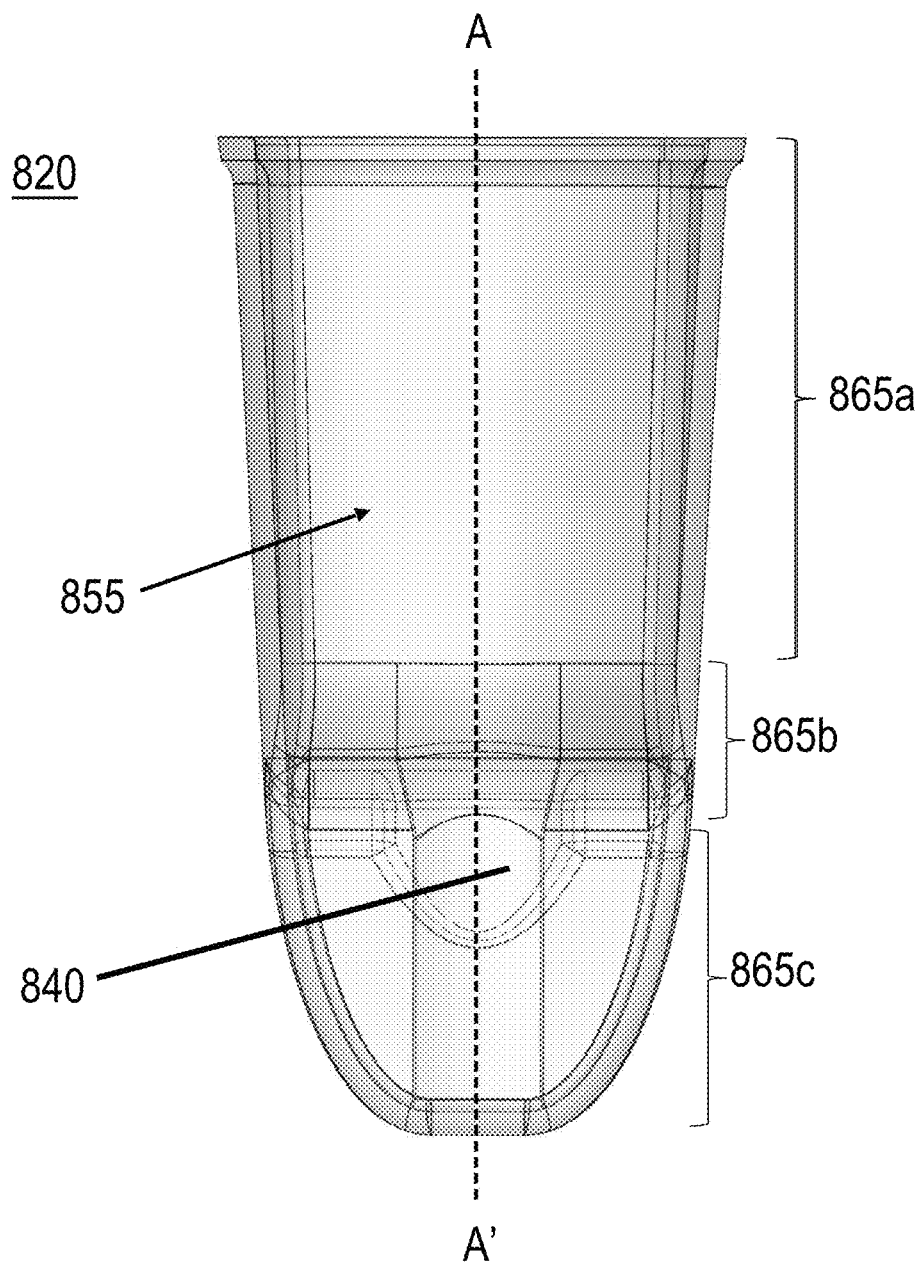
FIG. 8B illustrates a front view of the finger insert of FIG. 8A.
Figure 8C:
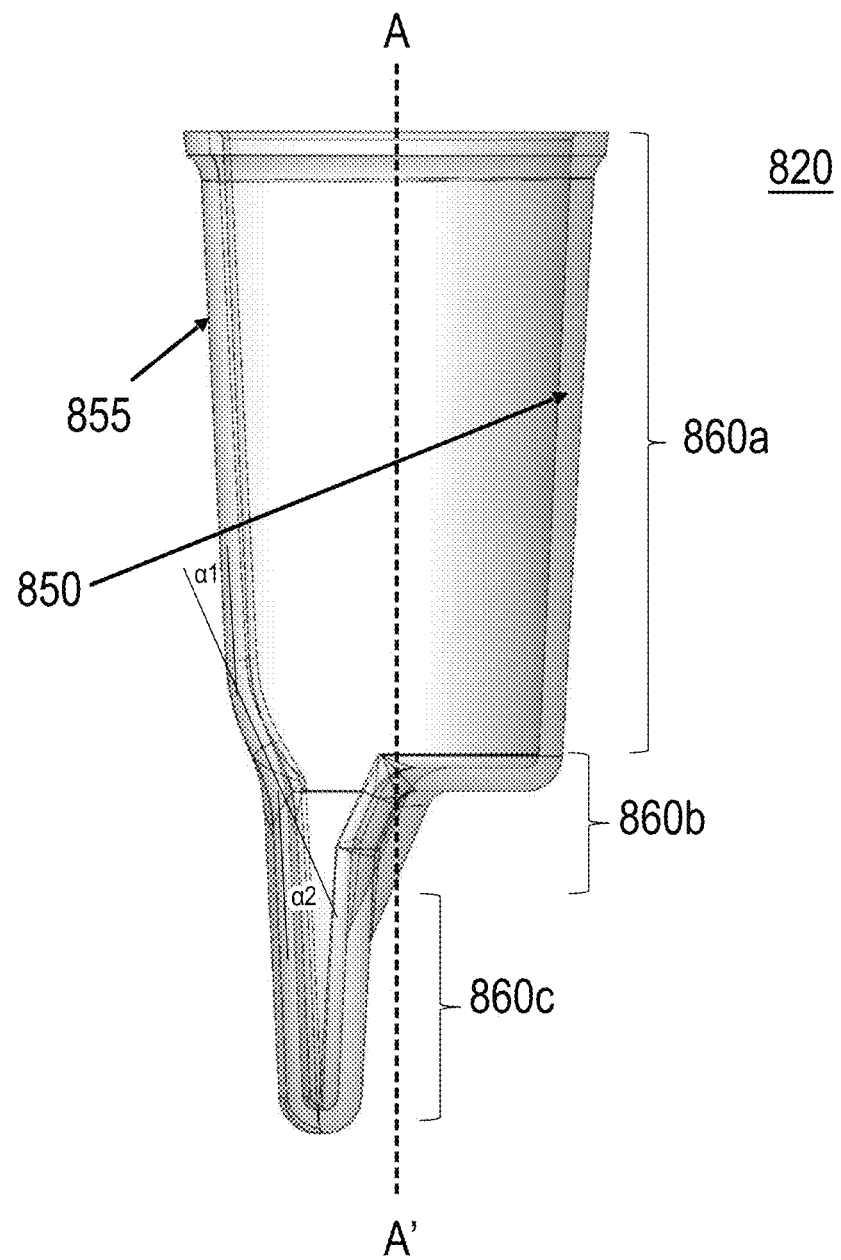
FIG. 8C illustrates a side view of the finger insert of FIG. 8A.
Figure 8D:
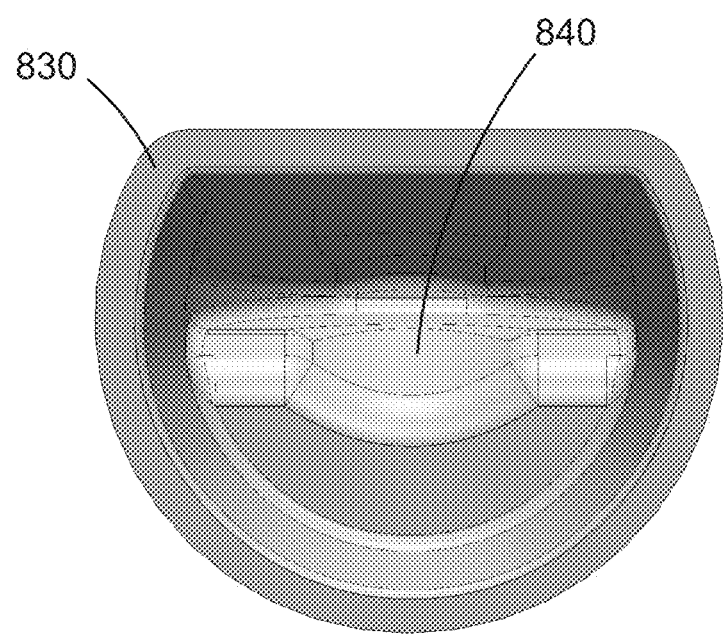
FIG. 8D illustrates a top view of the finger insert of FIG. 8A.

The housing 820 can be formed of a first wall 850 and a second wall 855, forming a fluid-tight seal as described above. The walls 855 can be integrally formed, or separately formed and fused, joined, glued, and/or otherwise combined together to yield the housing 820. The second wall 855, which can interface with imaging components (e.g., an illumination source, a detector, and/or the like) of a nailfold imaging device during use can be substantially optically transparent in the range of about 400 nm to about 800 nm, including all values and sub-ranges in between. In some cases, the first wall 850, and/or a portion thereof, can be substantially optically transparent as well. As explained in greater detail below, the walls 850, 855 can include various portions that accommodate a user's finger, and act in concert to maintain it in place, during use. The first wall 850 can be curved (e.g., round, elliptical, oval, parabolic, a curved spline, and/or the like) with respect to the axis A-A', as illustrated in FIGS. 8A-8C. The second wall 855 can be flat (e.g., sheet-like) with respect to the axis A-A'.

The first wall 850 can define a wall portion 860a, a wall portion 860b adjacent to the wall portion 860a, and a wall portion 860c adjacent to the wall portion 860b. The second wall portion can define a wall portion 865a, a wall portion 865b adjacent to the wall portion 865a, and a wall portion 865c adjacent to the wall portion 865b. These wall portions 865a, 865b, 865c, 860a, 860b, and 860c are sometimes also referred to here as a first wall portion, a second wall portion, a third wall portion, a fourth wall portion, a fifth wall portion, and a sixth wall portion, respectively. It is understood that while described as separate portions, any adjacent walls portions (e.g., the wall portions 865a, 865b) may be integrally formed such as, for example, via injection molding. In some cases, the entire housing 820 can be formed as a single piece via injection molding. In some cases, adjacent wall portions may be separately formed and fused, joined, glued, and/or otherwise combined together to form their respective wall.

Figure 9:
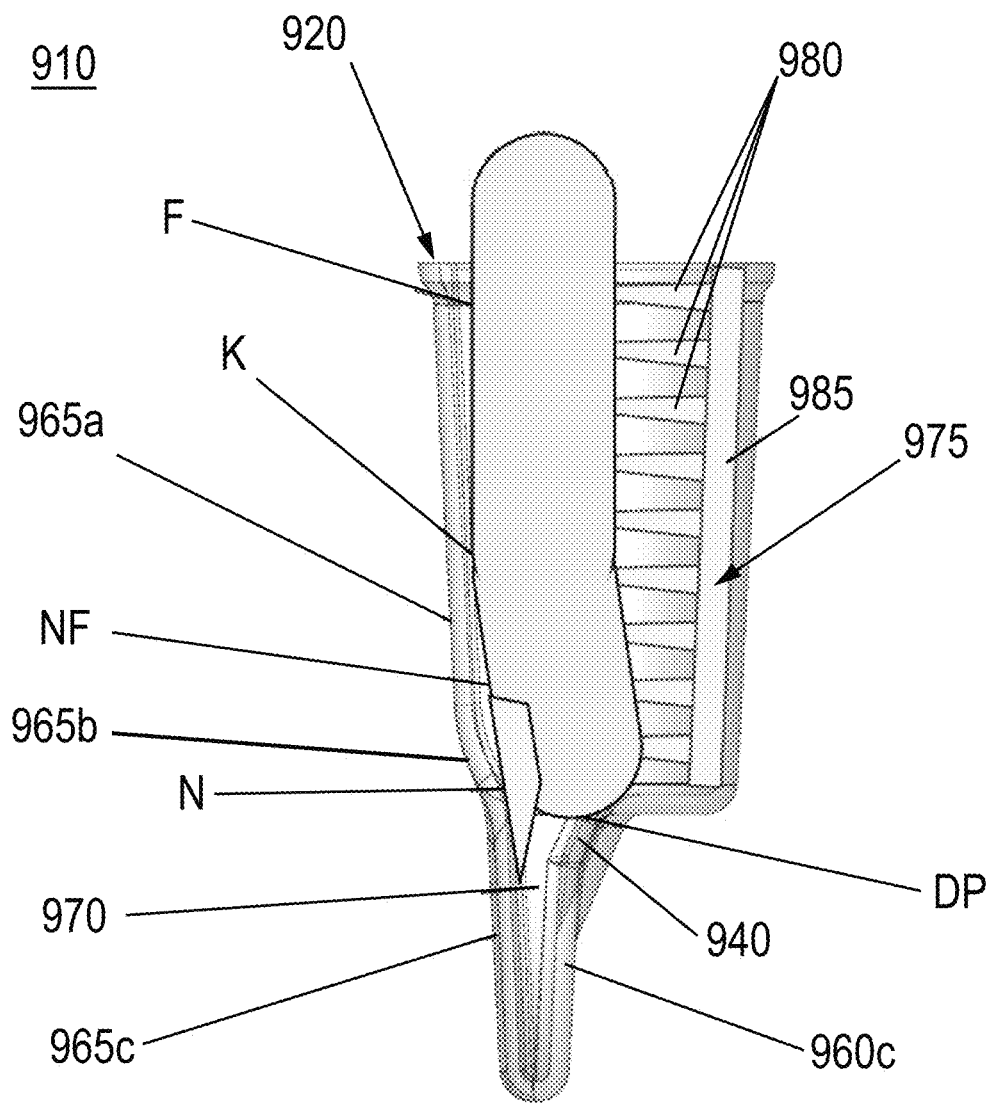
FIG. 9 illustrates a side view of the finger insert of FIG. 8A with a deformable pad, and with a user's finger inserted into the finger insert.

Referring to the second wall 855, an edge/side of the wall portion 865a can form a portion of the rim of the opening 830, as best illustrated in FIG. 8A. The wall portion 865a can be substantially optically transparent to permit imaging of the nailfold region of the user's finger. The wall portion 865*a* can be substantially flat in its entirety, or in part such as, for example, towards the wall portion 865*b*. During use a knuckle of the user's finger, e.g., the distal interphalangeal joint, can abut or lie against the wall portion 865*a*, as illustrated in FIG. 9 for the knuckle K, and described in greater detail later. The wall portion 865*a* can be angled with respect to, and/or form an angle with, the wall portion 865*b* at an angle α1, which can be about 10°, about 15°, about 20°, about 25°, about 30°, including all values and sub-ranges in between. The wall portion 865*c*, in turn can be angled with respect to, and/or form an angle with, the wall portion 865*b* at an angle α2, which can be about 10°, about 15°, about 20°, about 25°, about 30°, including all values and sub-ranges in between.

Referring to the first wall 850, an edge/side of the wall portion 860*a* can form a remaining portion of the rim of the opening 830, such that the wall portions 860*a*, 860*b* collective form and/or otherwise define the opening 830. As illustrated in FIGS. 8A-8C, the opening 830 can be generally circular, though in other cases (not shown), the opening 830 can be oval, elliptical, and/or the like. Factors affecting the shape of the opening 820 can include, but are not limited to, ease of holding, inserting, and/or removing the housing 820, ease of sealing the opening 820 with a fluid-tight seal, the shape of an opening of a receptacle in a finger insert device that receiving the insert 810, ease of fabrication (e.g., during injection molding), and/or the like.

As described above for the first wall 850 and as illustrated, the wall portion 860*a* can be curved. The cross-sectional area defined by the wall portion 860*a* can be substantially the same, or continuously decrease, from the opening 830 towards the wall portion 860*b*. The cross-sectional area can be, for example, about 2 cm$^2$ to about 4 cm$^2$ at the opening 830. In some cases, the cross-sectional area defined by the wall portion 860*a* can decrease in a periodic or step-wise manner, such that the wall portion 860*a* defines two or more different cross-sectional areas from the opening 830 towards the wall portion 860*b*. The wall portion 860*a* can be substantially optically transparent, e.g., similar to the wall portion 865*a*. In some cases, the wall portion 860*a* can be partially transparent, and/or composed of a light absorbing material, to prevent undesirable reflection of the excitation light during nailfold imaging. The wall portions 860*b*, 860*c* can collectively form and/or otherwise define the landing region that receives the end of the user's finger during use, as best illustrated in FIGS. 8A, 8C.

FIG. 9 illustrates a finger insert 910, which can be structurally and/or functionally similar to the finger insert 810, and generally shows the insert 910 during use, with a finger F of a user inserted through an opening 920. Unless expressly noted otherwise, similarly illustrated and labeled structures in FIG. 9 may be structurally and/or functionally similar to those in FIGS. 8A-8C such as, for example, the wall portion 965*a* can be similar to the wall portion 865*a*, and so on.

The insert 910 includes a pad 975 that is affixed, glued, and/or otherwise positioned on the first wall 850, e.g., wholly, or at least partly on the wall portion 860*a* of the first wall. The deformable pad 975 includes a base layer 985 and multiple spacers 980 formed on the base layer. In some cases, the base layer 985 can be absent, and the spacers 980 can be formed directly on the first wall 850. The pad 975 can be wholly deformable, e.g., both the base layer 985 and the spacers 980 can be composed of a deformable material such as, for example, silicone or a silicone-based material. In some cases, the base layer 985 and the spacers 980 can be composed of different materials of different deformability such as, for example, a silicone, a nitrile, a neoprene and/or other rubbers, combinations thereof, and/or the like. In other cases, the pad 975 can be partially deformable such as, for example, having the base layer 985 be composed of a rigid, inelastic material while the spacers 980 are composed of a deformable material.

The deformability of the spacers 980 can elastically deform upon insertion of the user's finger F, to press the finger F against the second wall 950. Each spacer 980 can be suitably shaped, sized, and laid out in an open-pore structure to maintain separation between adjacent spacers in the absence of deformation. Further, the open-pore structure of the spacers 980 can reduce the formation of air bubbles and/or generally reduce/eliminate any trapped air in the immersion liquid that may have entered the insert 910 during insertion or movement of the user's finger. Such trapped air can interfere with nailfold imaging and lead to artifacts.

The spacer 980 can be generally columnar or cylindrical in form, including forms such as, for example, right circular cylinders, oblique cylinders, cones, oblique cones, frustums (e.g., pyramidal, or conical), prismatic (e.g., elongated prisms, truncated elongated prisms, fin-like), and/or combinations thereof. As illustrated in FIG. 9, in some cases the spacers 980 can be substantially frustoconical in form, having a larger cross-sectional radius towards the base layer 985/the wall portion 975. The number of spacers can be 2, 10, 20, 50, 100, 150, 200, or more than 200, including all values and sub-ranges in between.

FIG. 9 also illustrates how the wall portions 960*c*, 965*c* cooperate to define and/or enclose a nail space 970 that can accommodate a nail N of the finger F. In this manner, the insert 910 can accommodate, i.e., receive in a secure fit manner, fingers of users with longer nails that extend beyond the distal end (i.e., the fingertip, also sometimes referred to as the distal phalange) of the user's finger.

Upon insertion of the finger F into the insert 910, the distal end DP of the finger lands and rests on the landing region 940, and is pushed against the wall 950 by the pad 980. By virtue of the angle α1 formed between the wall portions 965*a*, 965*b*, the knuckle/joint K of the finger lands on the wall portion 965*a*, while the nail N of the finger lands on the region 965*b*, resulting in a reduction of elimination of any interaction or contact between the wall portion 965*a* and the nailfold region NF of the finger F. This ensures that there is little, or no pressure applied on the region NF by the wall portion 965*a*, permitting blood to flow through the capillaries in the region NF, and in turn permitting imaging of the capillaries. In the absence of such angling between the wall portions 965*a*, 965*b*, the region NF would be compressed against the wall, resulting in blockage of flow in the capillaries of the region NF, and impeding nailfold imaging.

Referring now to the angle α2 formed between the wall portions 965*b*, 965*c*, allowing an angle of 10°-30° provides space for the lower extremity of the nail to protrude into nail space 970.

Figure 10A:
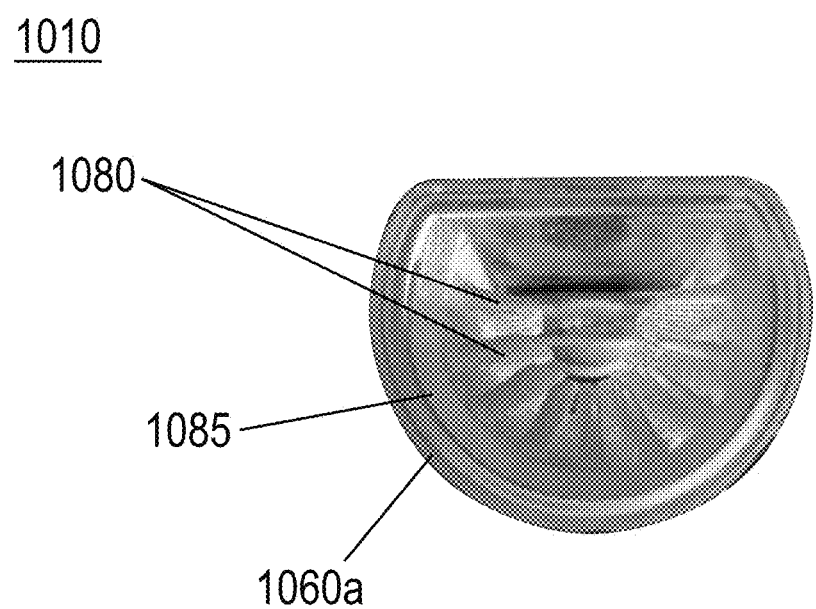
FIG. 10A shows a top view of an example finger insert similar to the finger insert of FIG. 8A.
Figure 10B:
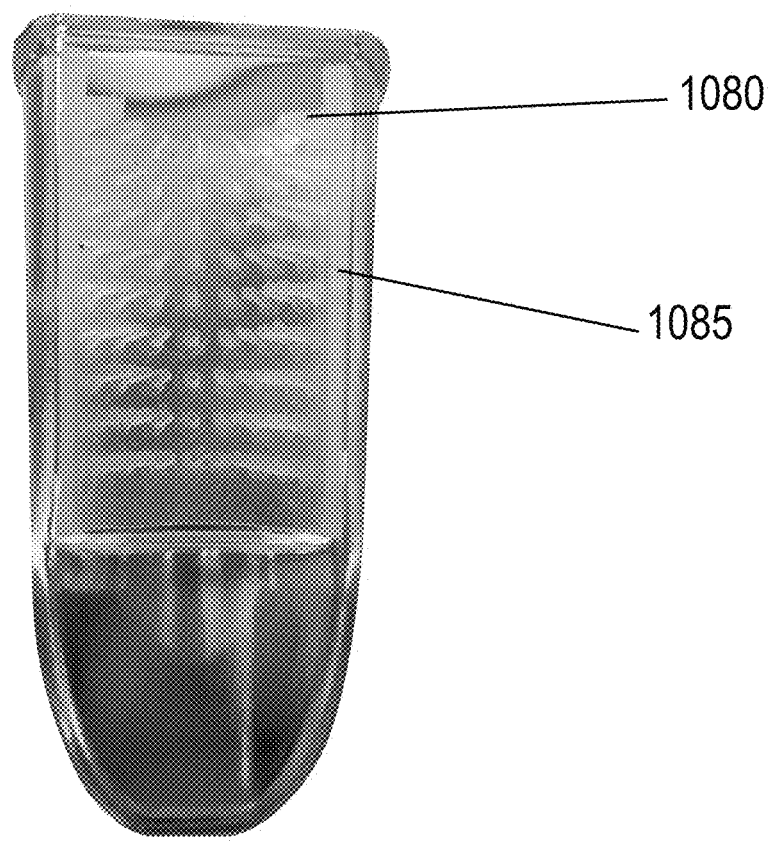
FIG. 10B shows a front view of the finger insert of FIG. 10A.

FIGS. 10A, 10B show a fabricated, example finger insert 1010 (e.g., structurally and/or functionally similar to the inserts 810, 910) with a deformable pad that includes both a base layer 1085 and spacers 1080 formed on the base layer. The base layer 1085 and the spacers 1080 here are integrally formed, of the same deformable material. The spacers 1080 are substantially conical in form. The finger insert 1010 is wholly transparent in this example, and the wall portion 1060*a* is substantially frustoconical, i.e., it has a decreasing cross-section area from the opening inwards.

Figure 11A:
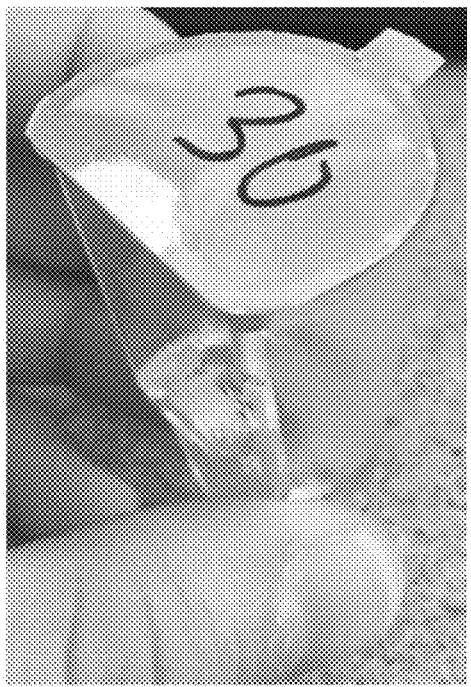
FIG. 11A shows an example finger insert with immersion oil and with a sealed opening.
Figure 11B:
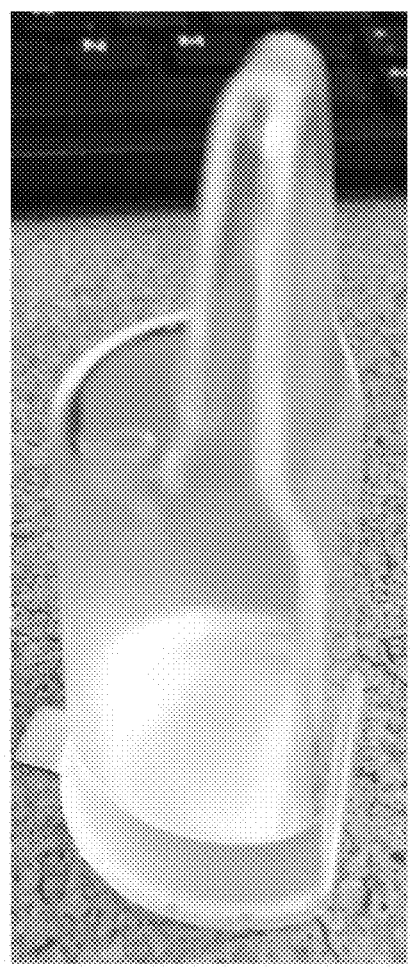
FIG. 11B is another view of the finger insert of FIG. 11A.
Figure 11C:
FIG. 11C is another finger insert similar to that of FIG. 11A, but different in at least one aspect.

FIGS. 11A-11C show various views of finger inserts (e.g., structurally and/or functionally similar to any of the inserts described herein) having immersion oil disposed therein, and a fluid-tight seal at the opening. The labeling, shown in FIGS. 11A and 11C, can indicate unit numbers and/or a scale associated with, for example, variation in geometry of the structures of the finger insert and/or the pad, volume and/or nature of the liquid contained within, and/or the like.

Figure 12:
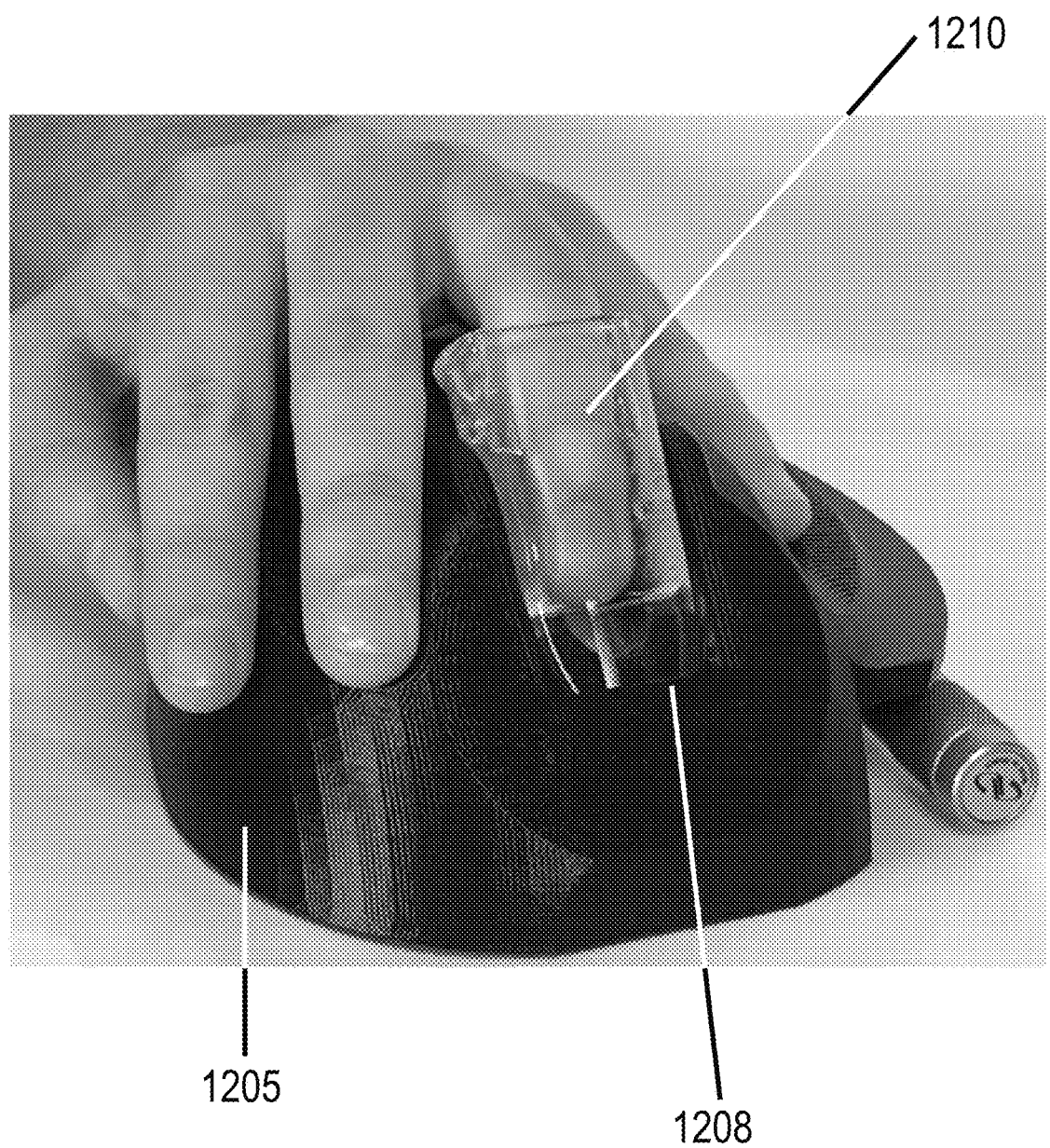
FIG. 12 shows an example finger insert, similar to the finger insert of FIG. 8A, positioned in a nailfold imaging device.

FIG. 12 shows a finger insert 1210 (e.g., structurally and/or functionally similar to the inserts described herein) during use with a nailfold imaging device 1205, and with a user's finger inserted therein. A receptacle 1208 of the device 1205 can receive the insert 1210 in a mating-fit manner. The device 1205 can be configured to perform nailfold imaging of the user's finger as generally described in the '038, '221 publications.

Aspects disclosed herein can be directed to kit that include multiple finger inserts (e.g., such as any finger insert described here). The finger inserts of the kit can be different from one other in any matter such as, but not limited to, a length of the housing along its longitudinal axis (e.g., along the axis A-A'), an average cross-sectional area of a curved wall portion (e.g., the wall portion 860a), variations in the geometry and/or mechanical properties of the pad (e.g., the pad 975). In some cases, each finger insert can have the liquid (e.g., a sterile immersion oil) already included therein, and a leak-proof covering over its opening, similar to shown in FIGS. 11A-11C. In some cases, the kit can include the nailfold imaging device itself, such as the device 1205, the device 1100 in FIG. 5, and/or as generally described in the '038, '221 publications. Such an imaging device, similar to that illustrated in FIG. 5 for example can include a light source to illuminate the nailfold region through the second wall (e.g., the wall 855), and a detector to receive the optical signal/beam from the nailfold region. The imaging device can also include a receptacle (e.g., the receptacle 1208) sized and shaped to receive the finger inserts in any suitable mating manner. In some cases, a system can include one or more finger inserts, and a nailfold imaging device as described herein.

Figure 13:
FIG. 13 illustrates a method for nailfold imaging.

FIG. 13 illustrates a method 1300, such as for nailfold imaging. The method 1300 includes, at 1310, receiving a finger of a user in a finger insert (e.g., structurally and the insert 810, 910, 1010, and/or 1210) disposed in a nailfold imaging device (e.g., the device of FIG. 5, FIG. 12, and/or as generally described in the '038, '221 publications). The finger insert can include a housing (e.g., the housing 820) that defines an opening (e.g., the opening 830) to receive a finger of a subject, and further defining a landing region (e.g., the region 840) that abuts against a distal phalange of the finger of the subject when the finger is placed into the finger insert via the opening. The housing can hold a liquid (e.g., an immersion oil) to facilitate imaging of a nailfold of the finger of the subject. In some cases, the method 1400 can encompass adding the liquid to the finger insert prior to step 1310.

At least the distal phalange of the finger is immersed in the liquid when the liquid is present in the finger insert and as the finger is placed into the finger insert via the opening. The housing including a first wall (e.g., the wall 850) and a second wall (e.g., the wall 855), the second wall being optically transparent to facilitate imaging of the nailfold of the finger. The method 1300 can also include inserting the finger insert into a receptacle of the nailfold imaging device. The nailfold imaging device includes a light source and a detector, and the receptacle includes an imaging window such that the light source and the detector are optically coupled to the imaging window.

The method also includes, at step 1320, imaging a nailfold portion of the finger via the wall portion of the finger insert using the nailfold imaging device. The imaging can include includes imaging the portion of the finger with the light source and detector via the imaging window and via the second wall of the finger insert.

It is understood that while described for imaging of nailfold regions in fingers of a user, aspects disclosed herein can be useful for imaging other portions of the body such as, for example, toes of the feet. As a non-limiting example, an insert for imaging a human toe can be shaped and sized according to the considerations laid out herein, and accounting for the specific anatomy of the human toe. One such consideration could be, for example, that toes of the human feet do not splay out to the same extent that fingers do, so a toe insert will likely have to be sized to prevent excessive and painful separation between the user's toes. Another consideration can be, for example, that toes display wider variability in size than fingers, so a toe insert may need to be designed specifically for one or fewer than all toes of a user's foot.

It is also understood that while described with respect to nailfold imaging, aspects disclosed herein can be useful for imaging other regions of a user's fingers outside the nailfold region (e.g., anywhere on the middle phalanx of the user's finger), other regions of a user's toes outside the nailfold region (e.g., anywhere on the middle phalanx of the user's finger or user's toe), and/or the like.

Example

Finger Positioning Study

Patient's fingers can be used to perform a number of different physiological and healthcare tests, including, for example, the noninvasive measurement of a patient's white blood cell or neutrophil levels. These measurements often require or depend on stabilizing the finger for a certain period of time, and keeping it repeatedly within a predefined Region of Interest (ROI) in order to successfully carry out the measurement. Demonstrated here is how a custom, disposable "finger insert" can meet these needs. A series of studies were on a sample size of nine naive subjects to estimate the critical target ROI for such blood measurements, as well as the intra-subject and inter-subject variability in finger positioning within that ROI. The focus was on tracking one particular finger anatomical location, the nailfold, and it was confirmed that the finger insert disposable can repeatedly position within a 7 mm by 5 mm ROI for 85% of the users. These studies demonstrate that the finger insert disposable can successfully centralize the nailfold within this defined ROI, therefore allowing its imaging through an optical system designed to cover such Field Of View (FOV). Analysis of the presented data additionally shows the capacity to collect data in a range of finger locations beyond the nailfold.

Introduction

The purpose of this study was to prove that an optical system with a FOV of 5 by 7 mm can consistently image the nailfold region (FIG. 14) of a set of naive users, across a variety of finger sizes, by employing a finger insert disposable as shown and described in FIGS. 10A, 10B. To do this, the focus was on the variability of the nailfold geometries across a range of different subjects. Typically, the ring finger of the user's non-dominant hand is measured, both in conventional video capillaroscopy, which is employed for a wide range of clinical applications, as well as in other recent techniques to noninvasively measure white blood cells. However, this study incorporates multiple fingers from each subject to replicate the geometric variability between fingers of a larger sample size. The goal was to prove successful imaging of nailfold ROIs across this larger sample size. Among the criteria for success was that naive users would be able to use the finger insert intuitively, that the finger can be placed comfortably into the finger insert, and that the nailfold should fall within the correct target zone or ROI for every measurement. To this end, the finger insert should guide the user's finger to the bottom extrusion within the finger insert as well as centering the finger and making the user comfortable. The knuckle of each finger measured should have minor contact with the inside face of the finger insert to stabilize the finger and avoid excessive pressure surrounding the nailfold, which could hinder blood flow and limit the ability to collect physiological and healthcare measurements from it. The ROI center should remain still to capture the measurement, so a padding in the finger insert was designed (the base layer 1085 and the spacers 1080 illustrated in FIGS. 10A, 10B) to secure the finger in place during the measurement with minimal vibration relative to the imaging system. The employed imaging system yields a 7 mm by 5 mm FOV, so the center of the ROI should be captured in this FOV.

In summary, this study aims at:
a. demonstrating an estimated range for the critical measurement ROI around a nailfold;
b. demonstrating imaging of the nailfold within a defined FOV across a range of finger sizes;
c. making the imaging and measurement work across all variations in finger geometry;
d. demonstrating that the finger insert disposable can work in the hands of naive users.

The criteria of a successful measurement considered here are:
a. the finger can be placed comfortably into the finger insert
b. the finger insert is intuitive to place the user's finger correctly (all the way down, touching the bottom/ landing region, and centered)
c. the finger insert improves the repeatability of finger placement
d. the nailfold should fall within the specified ROI every time
e. the finger insert padding prevents an upward force to minimize movement
f. the finger knuckle is pressed up against the insert in a way that does not exert excess pressure in the nailfold region, that would in turn restrict blood flow but keeps the finger stable
g. the center of the nailfold falls within a 5×7 mm ROI
h. the finger stays still +/−1 mm during a measurement
i. the finger insert provides for minimal vibration of the nailfold area relative to imaging system.

Methodology

Figure 14:
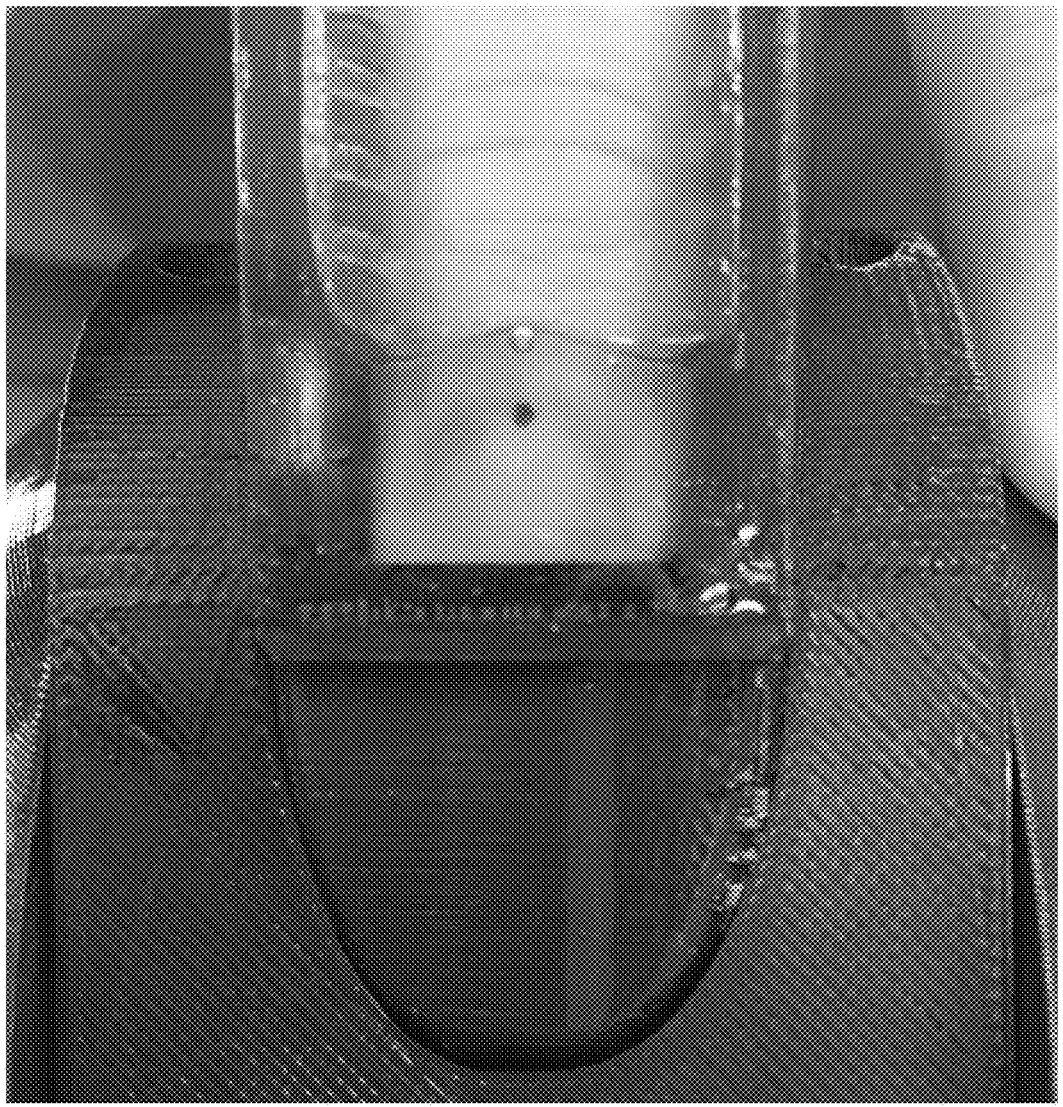
FIG. 14 shows how a user places their finger within a finger insert. The nailfold region is marked by a black dot placed at the center of the region.
Figure 15:
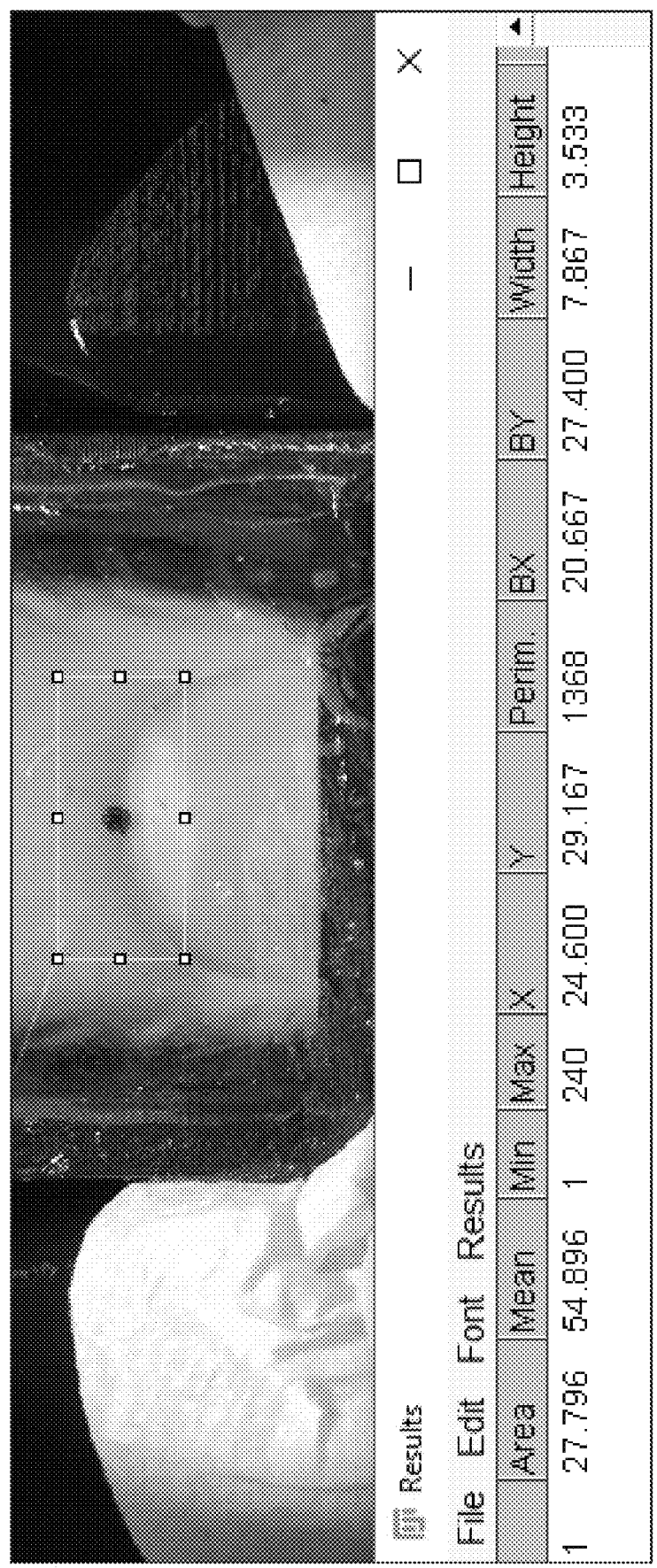
FIG. 15 illustrates an example of nailfold width and height calculation, done using the marked black dot as reference for the center of the nailfold.

This study was conducted to calculate each user's average nailfold ROI based on the sample of subjects. These subjects range in gender and age from 20 to 40 years old. The subjects' index, middle, and ring finger were studied five times each in every test as a means to examine more finger size and geometry varieties. The finger insert and camera were kept in a constant location throughout every picture. Using a marker, a trained operator manually placed a dot just above the users' nailfolds to identify the nailfold ROI center where the measurement occurs (FIG. 14). From these dot locations, the nailfold height and width were measured. Using ImageJ software, these ROI center locations were overlaid onto each other and graphed to better understand the range of finger sizes produced by the data (FIG. 15). The finger insert of FIGS. 10A, 10B was tested across nine subjects.

Results

Figure 16:
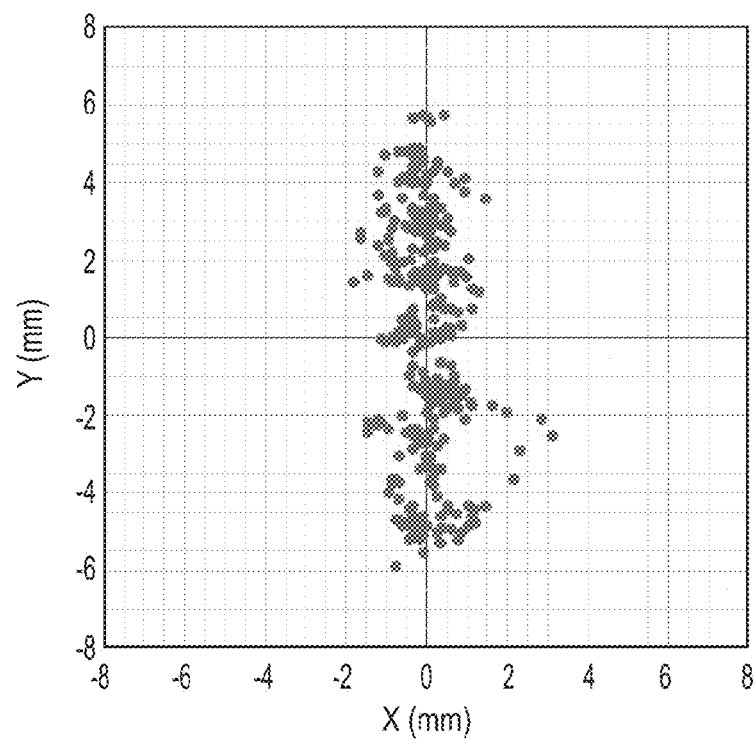
FIG. 16 is a plot demonstrating the variability between all subjects' nailfold ROI centers. The span is approximately 12 mm vertically and 5 mm horizontally.
Figure 17:
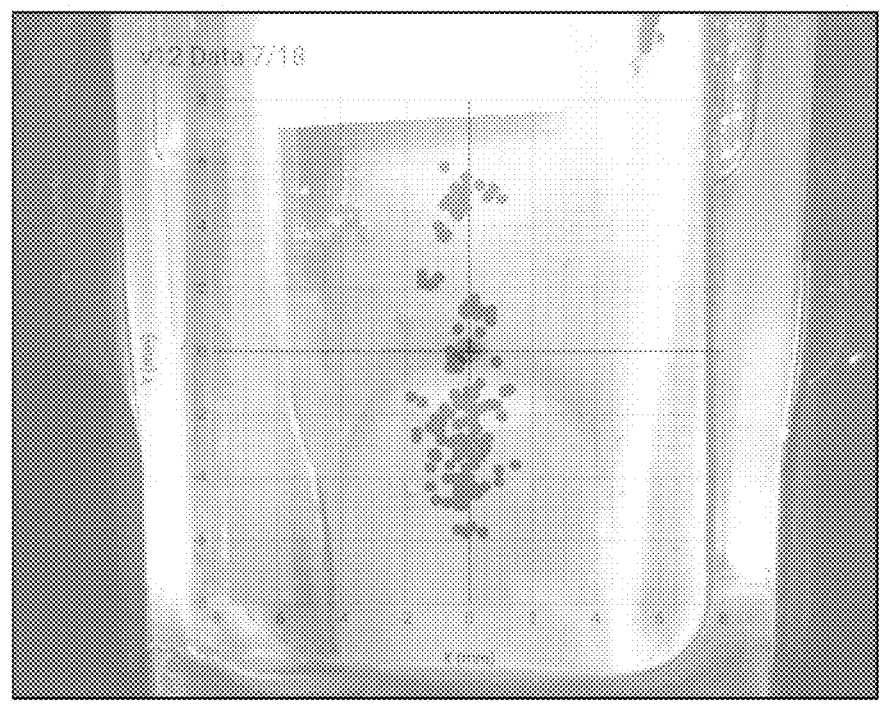
FIG. 17 illustrates an example data point from a particular subject's finger, with an approximate mapping of data distribution to an image of the finger in-place during one repeat.

Each dot on FIGS. 16, 17 represents one data point from one finger of each subject where the ROI center falls. The maximum range of data falls between about 12 mm in the vertical direction and roughly 5 mm in the horizontal direction across all subjects.

The data indicates that the finger insert condenses the nailfold ROI centers of the sample size to a range where one can take measurements with confidence. Based on measuring the center of the nailfold, it was found that each finger has roughly a 2 by 2 mm span for repeatability on the same location, as discernable from FIGS. 18, 19. By taking the center of the nailfold and measuring outwards until the end of the nailfold (FIG. 15), the study found that the average width of nailfolds is 8.2 mm among the subjects. There is a minimal amount of translation in the vertical direction due to the geometry of the common nailfold.

Figure 18:
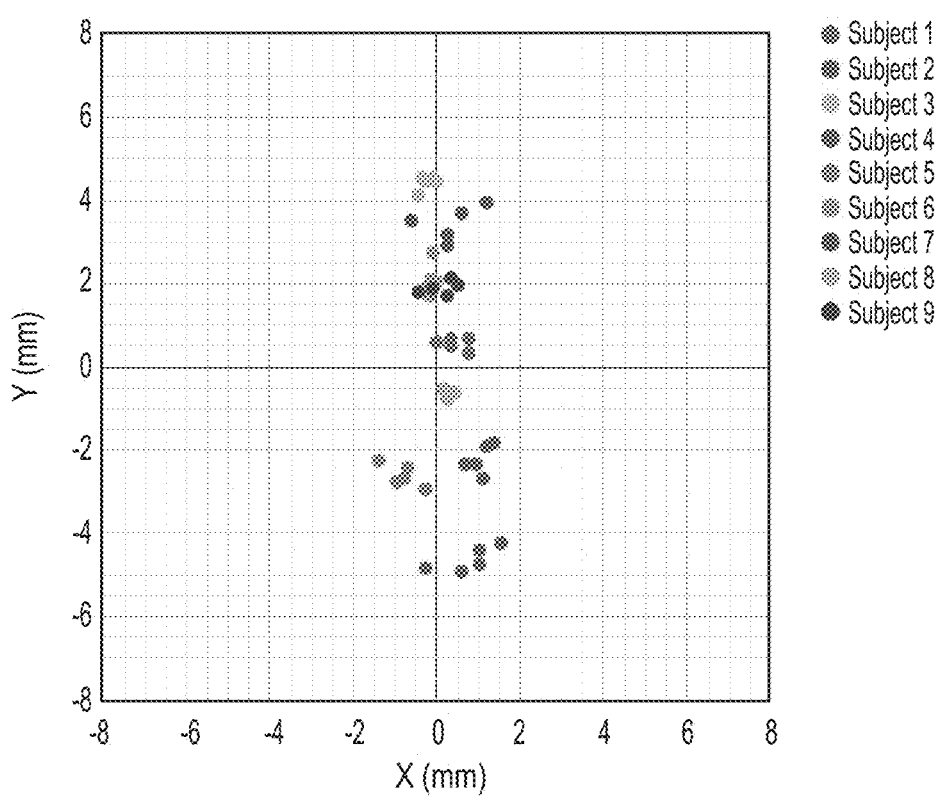
FIG. 18 is a plot illustrating five data points from each subject's ring finger on their right hand. It also illustrates the range of finger-tip lengths and slight asymmetries of each specific finger of a user, and the variation in movement between that one finger's repetitive insertion into the finger insert.
Figure 19:
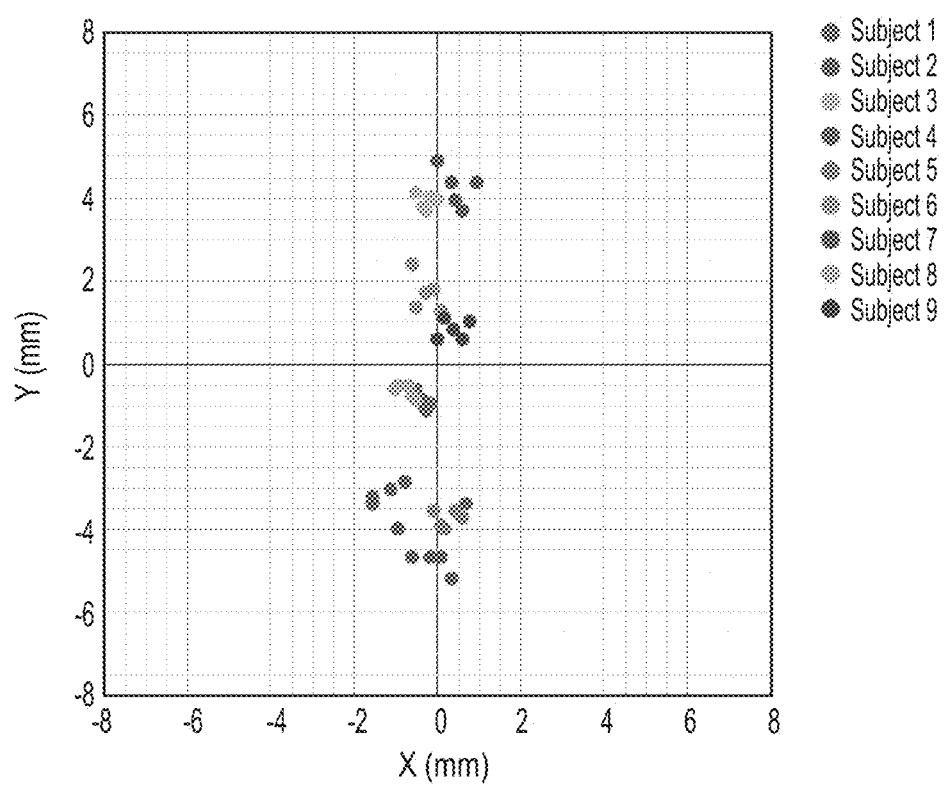
FIG. 19 is a plot illustrating five data points from each subject's ring finger on their left hand. It also illustrates the range of finger-tip lengths and slight asymmetries of each specific finger of a user, and the variation in movement between that one finger's repetitive insertion into the finger insert.
Figure 20:
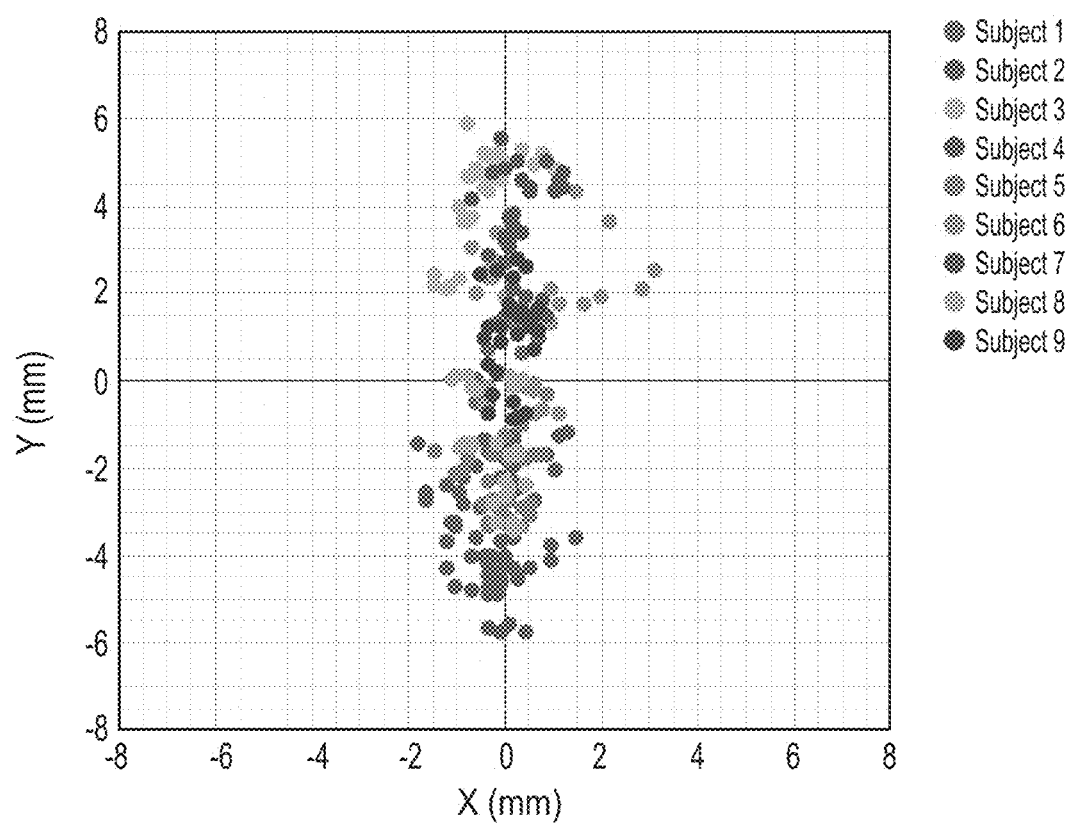
FIG. 20 is a plot illustrating all data points from the plots of FIGS. 18, 19, by subject. Intra-subject data shows the variation across different fingers of that subject.
Figure 21:
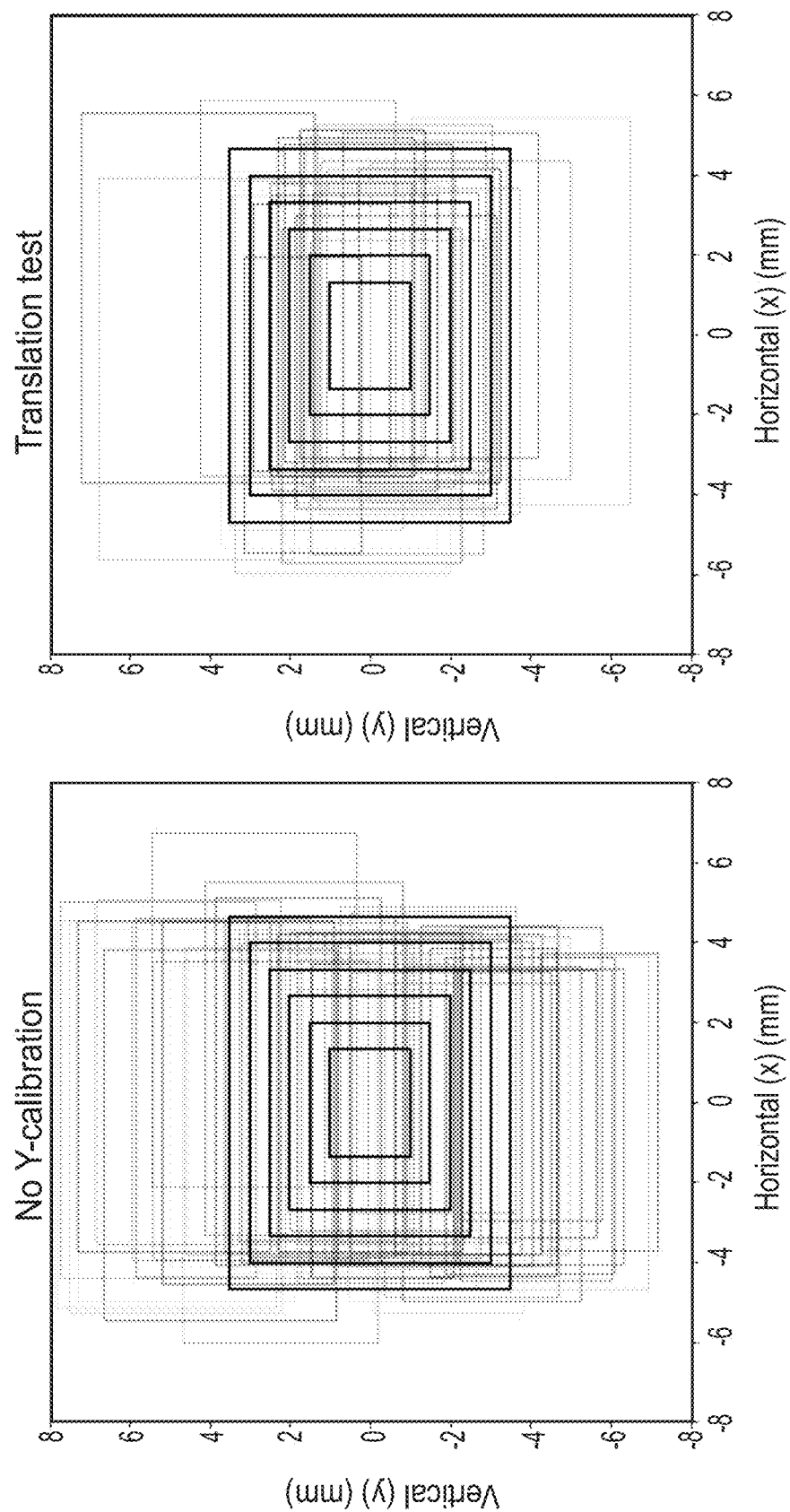
FIG. 21 illustrates the nailfold ROI of all the subjects overlaid on each other, while the black boxes are the different FoVs at the time. Specifically, the left plot illustrates the free positioning of the nailfolds ROIs, while the right plot illustrates a similar study where the vertical position of the finger insert in the receiving device was pre-calibrated by a measurement of the length of the finger-tip to nailfold, demonstrating a reduction in the variation in ROI positions across multiple users and fingers.

In conclusion, variability was present within the test, but the data condenses to approximately 2 mm by 1 mm (FIGS. 18, 19). Intra-subject data shows about a 4-5 mm variation in the Y-direction across the index, middle, and ring fingers (FIG. 20). The most dispersed data corresponded to the left middle finger of one particular subject, and all data points fall within 4 mm by 3 mm FoV. The largest ROI encompassing all finger positions from our data was about 9.5 mm by 5.5 mm, and the largest FoV where one could image the nailfold area was 8 mm by 6 mm (FIG. 21). By using pre-calibration, that is, by adjusting the Y position of the finger disposable beforehand to compensate for each user's finger length, we can image most nailfold areas within an 8 mm by 6 mm FoV.

Conclusion

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All publications, patent applications, patents, and other references mentioned herein are incorporated by reference in their entirety.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of" or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A system, comprising:
   a finger imaging device, including:
   a light source;
   a detector;
   a receptacle including an imaging window, the light source and the detector optically coupled to the imaging window; and
   a finger insert, the finger insert being disposable in the receptacle, including:
      a housing defining an opening adapted to receive a finger of a subject, and further defining a landing region adapted to abut against a distal phalange of the finger of the subject when the finger is placed into the finger insert via the opening, to hold a liquid to facilitate imaging of a nailfold of the finger of the subject, wherein at least the distal phalange of the finger is immersed in the liquid when the liquid is present in the finger insert and as the finger is placed into the finger insert via the opening, the housing including a first wall and a second wall, the second wall being optically transparent to facilitate imaging of the nailfold of the finger via the light source and detector, such that at least a section of the second wall is in optical communication with the imaging window when the finger insert is disposed in the receptacle; and
      a deformable pad positioned on at least a portion of the first wall, adapted to form an open-pore structure that fills a gap between the first wall and the finger of the user when the finger is inserted into the finger insert, and adapted to reduce trapped air in the liquid when the liquid is present in the finger insert, during insertion and movement of the finger in the finger insert.

2. The system of claim 1, the second wall defining:
   a first wall portion defining a portion of the opening, adapted to abut against a distal interphalangeal joint of the finger of the subject;
   a second wall portion adjacent to the first wall portion and angled with respect to the first wall portion; and
   a third wall portion adjacent to the second wall portion and angled with respect to the third wall portion,
   such that the second wall portion, the third wall portion, or both, are adapted to abut against the nail of the finger of the user, to prevent or reduce contact between the nailfold and the second wall.

3. The system of claim 2, the first wall defining:
a fourth wall portion defining a reminder portion of the opening and having the deformable pad coupled thereto;
a fifth wall portion adjacent to the fourth wall portion; and
a sixth wall portion adjacent to the fifth wall portion,
such that the fifth wall portion and the sixth wall portion collectively define the landing region adapted to receive the distal phalange of the finger of the subject during use.

4. The system of claim 3, wherein the third wall portion and the sixth wall portion collectively define a nail space adapted to accommodate a portion of the nail of the finger that extends beyond the distal phalange of the finger during use.

5. The system of claim 3, wherein the first wall portion is flat, and wherein the fourth wall portion is curved.

6. The system of claim 5, wherein a cross-sectional area of the fourth wall portion continuously decreases from the opening of the housing to the fifth wall portion.

7. The system of claim 5, wherein the fourth wall portion has two or more different cross-sectional areas along a longitudinal axis of the housing.

8. The system of claim 5, wherein the deformable pad includes a plurality of deformable spacers to elastically deform upon insertion of the finger into the finger insert, wherein each deformable spacer is shaped and sized to maintain separation between adjacent deformable spacers of the plurality of deformable spacers in the absence of finger insertion.

9. The system of claim 3, wherein the fourth wall portion is optically transparent.

10. The system of claim 3, wherein a cross-sectional area of the opening is from about 2 cm$^2$ to about 4 cm$^2$.

11. The system of claim 1, wherein the housing is composed of an inelastic material.

12. The system of claim 1, a length of the housing along its longitudinal axis being from about 1 cm to about 7 cm.

13. The system of claim 1, wherein the deformable pad includes a plurality of deformable spacers to elastically deform upon insertion of the finger into the finger insert.

14. The system of claim 13, wherein the deformable pad further includes a base layer having the plurality of deformable spacers formed thereon.

15. The system of claim 13, wherein the plurality of deformable spacers includes 2 to 200 deformable spacers.

16. The system of claim 13, the plurality of deformable spacers being composed of a material including a silicone.

17. The system of claim 1, wherein the finger insert is composed of a substantially rigid material.

18. A kit, comprising:
a finger imaging device, including:
  a light source;
  a detector; and
  a receptacle including an imaging window, the light source and the detector optically coupled to the imaging window; and
a set of finger inserts, each finger insert of the set of finger inserts including:
  a housing defining an opening adapted to receive a finger of a subject, and further defining a landing region adapted to abut against a distal phalange of the finger of the subject when the finger is placed into the finger insert via the opening, to hold a liquid to facilitate imaging of a nailfold of the finger of the subject, wherein at least the distal phalange of the finger is immersed in the liquid when the liquid is present in the finger insert and as the finger is placed into the finger insert via the opening, the housing including a first wall and a second wall, the second wall being optically transparent to facilitate imaging of the nailfold of the finger; and
  a deformable pad positioned on at least a portion of the first wall, adapted to form an open-pore structure that fills a gap between the first wall and the finger of the subject when the finger is inserted into the finger insert, and adapted to reduce trapped air in the liquid when the liquid is present in the finger insert, during insertion and movement of the finger in the finger insert,
each finger insert of the set of finger inserts being disposable in the receptacle such that at least a section of the second wall of that finger insert is in optical communication with the imaging window when that finger insert is disposed in the receptacle,
wherein a first finger insert of the set of finger inserts is different from a second finger insert of the set of finger inserts in one or more of:
  a length of the housing along its longitudinal axis; and
  an average cross-sectional area of a curved portion of the first wall.

19. The kit of claim 18, wherein the housing of each finger insert of the set of finger inserts is composed of a substantially rigid material.

20. A method, comprising:
receiving a finger of a user in a finger insert disposed in a finger imaging device, the finger insert including:
  a housing defining an opening adapted to abut receive a finger of a subject, and further defining a landing region adapted to abut against a distal phalange of the finger of the subject when the finger is placed into the finger insert via the opening, to hold a liquid to facilitate imaging of a nailfold of the finger of the subject, wherein at least the distal phalange of the finger is immersed in the liquid when the liquid is present in the finger insert and as the finger is placed into the finger insert via the opening, the housing including a first wall and a second wall, the second wall being optically transparent to facilitate imaging of the nailfold of the finger, the finger insert being disposed in a receptacle of the imaging device such that at least a section of the second wall of that finger insert is in optical communication with the imaging window when that finger insert is disposed in the receptacle; and
  a deformable pad positioned on at least a portion of the first wall, adapted to form an open-pore structure that fills a gap between the first wall and the finger of the user when the finger is inserted into the finger insert, and adapted to reduce trapped air in the liquid when the liquid is present in the finger insert, during insertion and movement of the finger in the finger insert; and
imaging a nailfold portion of the finger via the wall portion of the finger insert using the nailfold imaging device.

21. The method of claim 20, further comprising:
inserting the finger insert into the receptacle of the finger imaging device, the finger imaging device including a light source and a detector, the receptacle including an imaging window, wherein the light source and the detector are optically coupled to the imaging window, wherein the imaging includes imaging the portion of the finger with the light source and detector via the imaging window and via the second wall of the finger insert.

22. The method of claim 20, further comprising adding the liquid to the finger insert prior to the receiving.

23. The method of claim 20, wherein the liquid includes an immersion oil.

\* \* \* \* \*